(12) United States Patent
Desai et al.

(10) Patent No.: US 10,899,713 B2
(45) Date of Patent: Jan. 26, 2021

(54) PROCESS FOR THE PREPARATION OF QUINOLONE BASED COMPOUNDS

(71) Applicant: CADILA HEALTHCARE LIMITED, Gujarat (IN)

(72) Inventors: Ranjit C. Desai, Gujarat (IN); Rajiv Sharma, Gujarat (IN); Vrajesh Pandya, Gujarat (IN); Kalpesh Shah, Gujarat (IN); Sunil Patel, Gujarat (IN); Rakesh Chauhan, Gujarat (IN); Ranjeet Nair, Gujarat (IN); Vivek Joshi, Gujarat (IN); Manoj Patel, Gujarat (IN); Mrigendra Shukla, Gujarat (IN)

(73) Assignee: CADILA HEALTHCARE LIMITED, Gujarat (IN)

( * ) Notice: Subject to any disclaimer, the term of this patent is extended or adjusted under 35 U.S.C. 154(b) by 0 days.

(21) Appl. No.: 16/421,671

(22) Filed: May 24, 2019

(65) Prior Publication Data

US 2019/0359574 A1    Nov. 28, 2019

(30) Foreign Application Priority Data

May 25, 2018 (IN) .............................. 201821019633
Dec. 29, 2018 (IN) .............................. 201821049821

(51) Int. Cl.
*C07D 215/58* (2006.01)
*C07D 215/56* (2006.01)

(52) U.S. Cl.
CPC ......... *C07D 215/58* (2013.01); *C07D 215/56* (2013.01)

(58) Field of Classification Search
CPC .......................... C07D 215/58; C07D 215/56
See application file for complete search history.

(56) References Cited

U.S. PATENT DOCUMENTS

| | | | |
|---|---|---|---|
| 2004/0087577 A1* | 5/2004 | Pratt | C07D 495/04 514/222.8 |
| 2004/0097492 A1* | 5/2004 | Pratt | C07D 215/22 514/222.8 |
| 2004/0162285 A1* | 8/2004 | Pratt | C07D 417/14 514/223.2 |
| 2004/0167123 A1* | 8/2004 | Pratt | C07D 471/04 514/223.2 |

* cited by examiner

*Primary Examiner* — Timothy R Rozof
(74) *Attorney, Agent, or Firm* — Ladas & Parry LLP

(57) ABSTRACT

The present invention relates to an improved process for the preparation of quinolone based compounds of general formula (I) using intermediate compound of general formula (XII). Invention also provides an improved process for the preparation of compound of formula (I-a) using intermediate compound of formula (XII-a) and some novel impurities generated during process. Compounds prepared using this process can be used to treat anemia.

55 Claims, 1 Drawing Sheet

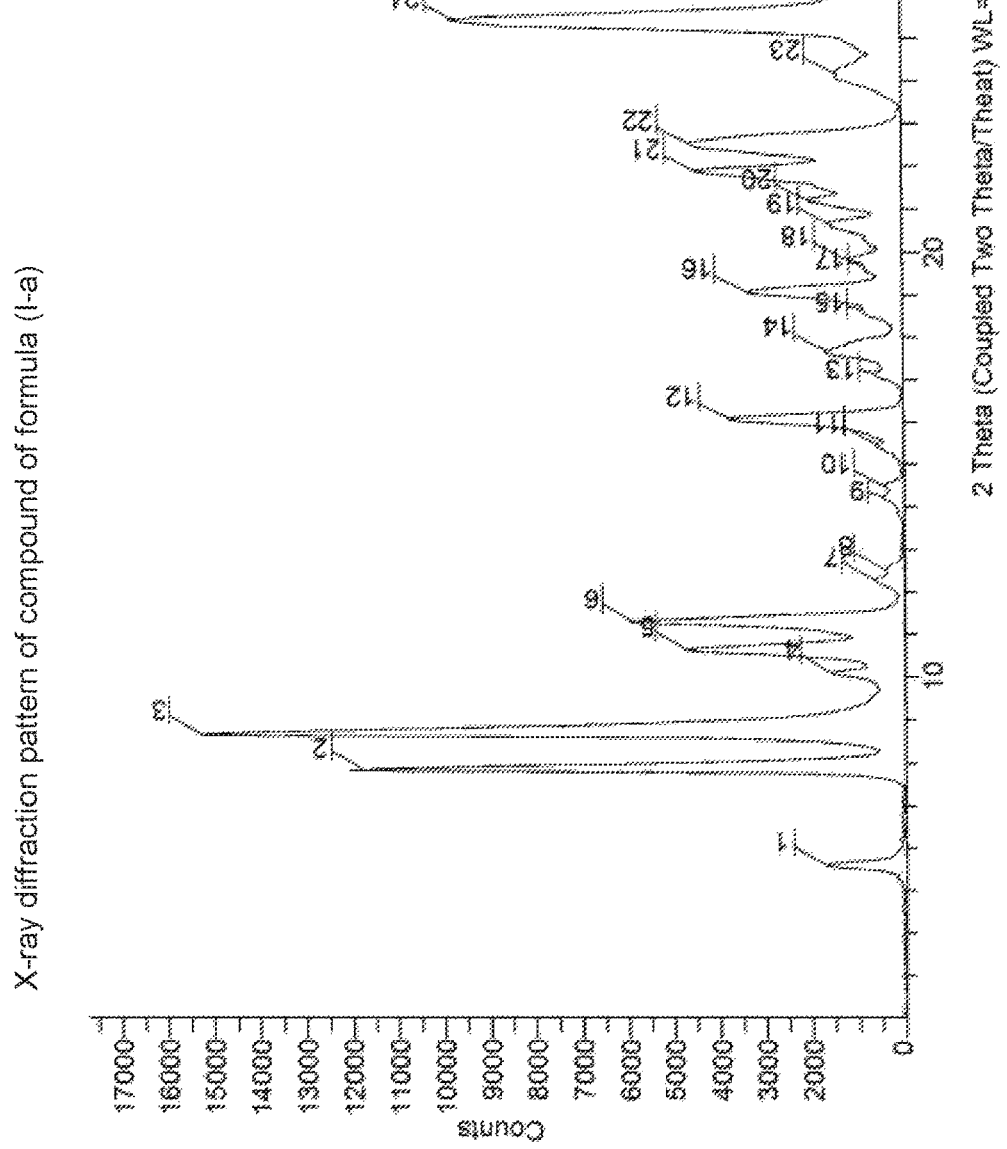

PROCESS FOR THE PREPARATION OF QUINOLONE BASED COMPOUNDS

FIELD OF THE INVENTION

The present invention relates to an improved process for the preparation of quinolone based compounds of general formula (I) using intermediate compound of general formula (XII). More specifically invention provides an improved process for the preparation of compound of formula (I-a) using intermediate compound of formula (XII-a). Invention also provides some novel impurities generated during process.

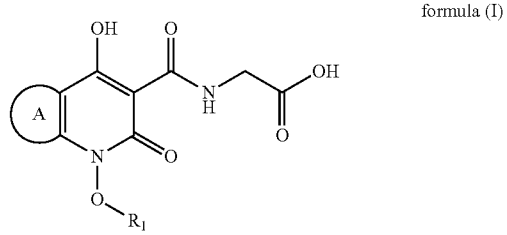

formula (I)

BACKGROUND OF INVENTION

Patent applications WO 2004041818, US 20040167123, US 2004162285, US 20040097492 and US 20040087577 describes the utility of N-arylated hydroxylamines of formula (IV), which are intermediates useful for the synthesis of certain quinolone derivatives (VI) as inhibitors of hepatitis C (HCV) polymerase useful for the treatment of HCV infection. In these references, the compound of formula (IV) was prepared using Scheme 1 which involves partial reduction of nitro group and subsequent O-alkylation using sodium hydride as a base.

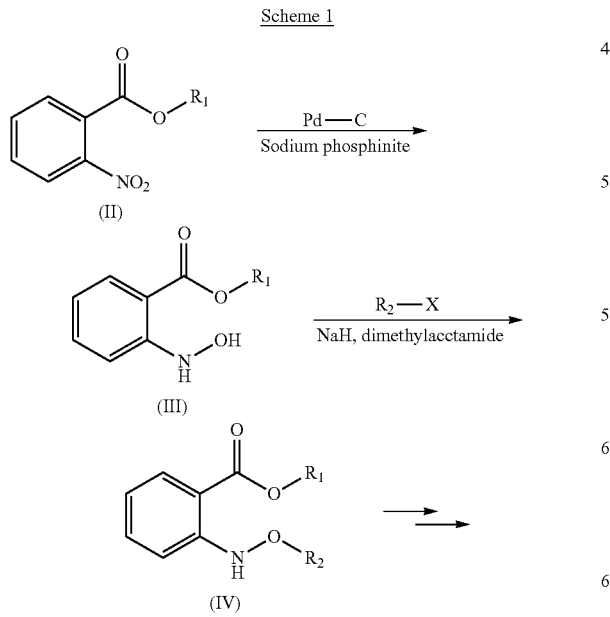

The patent application WO 2014102818 describes the use of certain quinolone based compound of formula (I) as prolyl hydroxylase inhibitors for the treatment of anemia. Compound of formula (I) was prepared according to scheme 2 which involved partial reduction of nitro group and subsequent O-alkylation using cesium carbonate as a base.

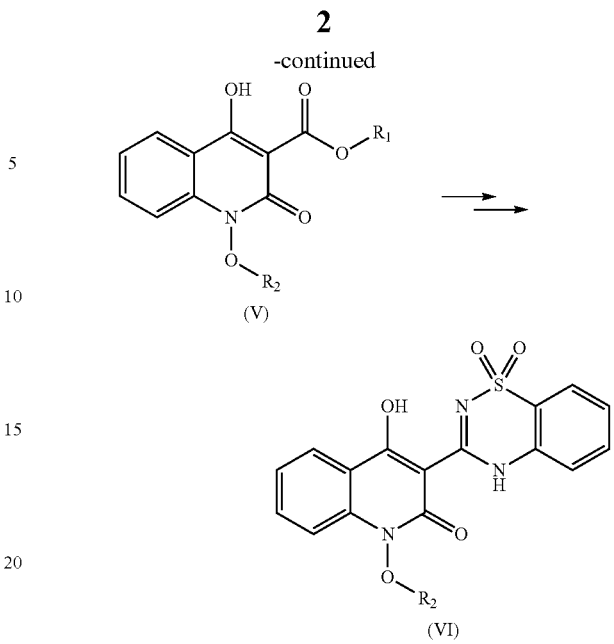

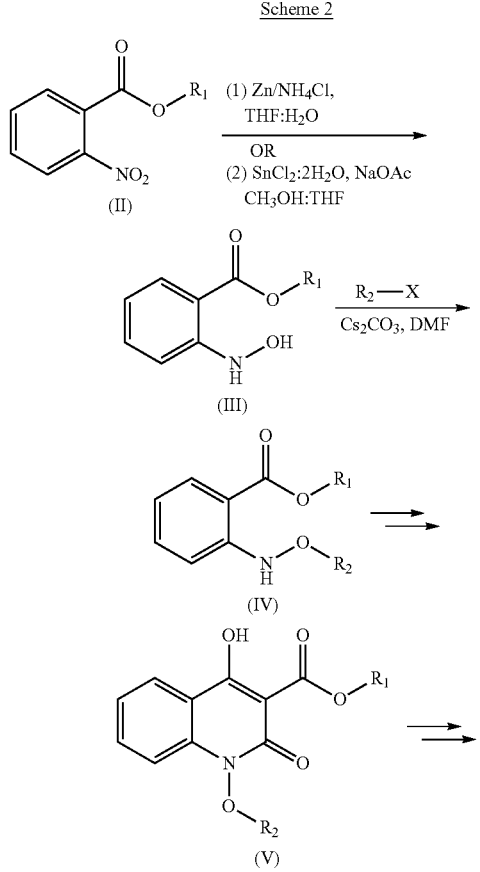

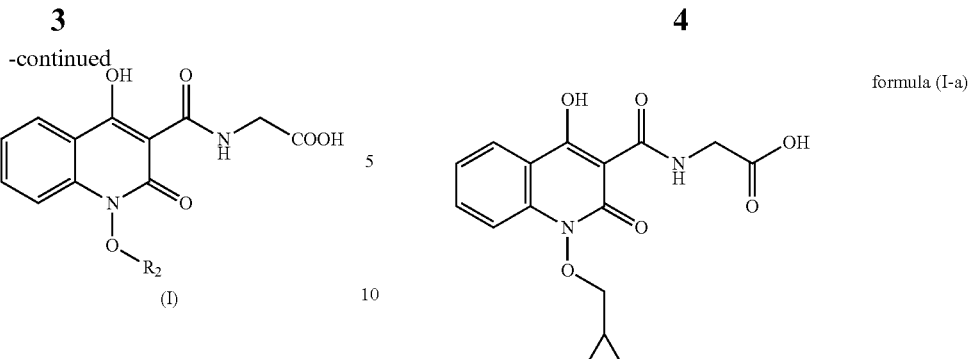

formula (I-a)

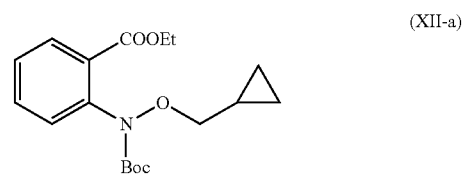

The drawback of process disclosed in WO 2014102818 (Scheme 2) is that it teaches usage of many hazardous reagents and process requires column chromatographic purification using highly flammable solvent at one of the stage and purification at multi steps during synthesis, which is not feasible for bulk production.

Further, N-arylated hydroxylamines compounds represent an important intermediate (compounds of formula (VI)) for the synthesis of compounds with diversified biological activities. However, there is still need for an improved process for the preparation of N-arylated hydroxylamine compounds of formula (VI) and intermediates thereof.

SUMMARY OF THE INVENTION

The present invention discloses an improved process for the preparation of quinolone based compounds of general formula (I) using intermediate compound of general formula (XII). More specifically invention provides an improved process for the preparation of compound of formula (I-a) using intermediate compound of formula (XII-a). Invention also provides some novel compounds which are impurities generated during process. The compounds prepared by this method are useful for the treatment of anemia.

DESCRIPTION OF DRAWINGS

FIG. 1 is the Powder X-ray Diffraction pattern of (1-(cyclopropylmethoxy)-4-hydroxy-2-oxo-1,2-dihydroquinoline-3-carbonyl)glycine (compound I-a).

EMBODIMENTS OF THE INVENTION

In one of the embodiment, there is provided a process for the preparation of compound of formula (I) using intermediate compounds of formula (XII).

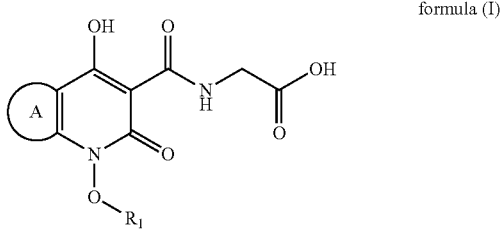

formula (I)

In other embodiment, there is provided a process of preparation of intermediate compound of formula (XII).

In another embodiment there is provided a process for the preparation of compound of following formula (I-a) using intermediate compound of formula (XII-a).

In another embodiment there is provided a compound of formula (XII-a).

In yet another embodiment there is provided a process for the preparation of compound (XII-a).

In an embodiment is provided a crystalline form of compound of formula (I-a).

In another embodiment, the invention encompasses compounds having chemical name 2-(2-(1-(cyclopropylmethoxy)-4-hydroxy-2-oxo-1,2-dihydroquinoline-3-carboxamido)acetamido)acetic acid (Compound XVII), chemical name (1-(cyclopropylmethyl)-4-hydroxy-2-oxo-1,2-dihydroquinoline-3-carbonyl)glycine (Compound XVIII) and chemical name (1-butoxy-4-hydroxy-2-oxo-1,2-dihydroquinoline-3-carbonyl)glycine (Compound XIX). These compounds were formed as impurities during the process of preparing the compound of formula (I-a).

In an embodiment the compound of formula (XVII) is controlled in formula (I-a) with the limit of 0.01% to 2.0%.

In another embodiment the compound of formula (XVIII) is controlled in formula (I-a) with the limit of 0.01% to 2.0%.

In an embodiment the compound of formula (XIX) is controlled in formula (I-a) with the limit of 0.01% to 2.0%.

In another embodiment, the invention is directed to a process for synthesizing compounds of XVII, XVIII and XIX.

DESCRIPTION OF THE INVENTION

List of Abbreviations

DABCO: 1,4-Diazabicyclo[2.2.2]octane
DBN: 1,5-Diazabicyclo[4.3.0]non-5-ene
DBU: 1,8-Diazabicyclo[5.4.0]undec-7-ene
DIPEA: Diisopropyl ethyl amine
DMF: Dimethyl formamide
DCM: Dichloromethane
DMSO: Dimethyl sulfoxide
DMSO-d6: Hexadeuterodimethyl sulfoxide
HCl: Hydrochloric acid
IPA: Isopropyl alcohol
$K_2CO_3$: Potassium carbonate
MTBE: Methyl tert-butyl ether NaCl: Sodium chloride
Na$_2$SO$_4$: Sodium sulfate
NaH: Sodium Hydride
NaHCO$_3$: Sodium bicarbonate
NaOH: Sodium hydroxide
NMP: N-methyl-2-pyrrolidone
POCl$_3$: Phosphoryl chloride/Phosphorous oxychloride
TFA: Trifluoro acetic acid
THF: Tetrahydrofuran
$^1$H NMR: Proton Nuclear Magnetic Resonance
h: Hour(s)
RT: room temperature [25-30° C.]
min: Minute(s)

Definitions

The aryl group used either alone or in combination with other radicals, is selected from a suitable aromatic system containing one two or three rings wherein such ring may be attached together in pendant manner or may be fused, more preferably the groups are selected from optionally substituted phenyl, naphthyl, tetrahydronaphthyl, biphenyl and the like.
the 'alkyl' group either used alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;
the 'cycloalkyl' group used either alone or in combination with other radicals, is selected from a cyclic radical containing three to six carbons, more preferably cyclopropyl, cyclobutyl, cyclopentyl, cyclohexyl, and the like;
the 'cycloalkenyl' group used either alone or in combination with other radicals, are preferably selected from cyclopropenyl, 1-cyclobutenyl, 2-cyclobutenyl, 1-cyclopentyl, 3-cyclopentyl, 1-cyclohexenyl, 2-cyclohexenyl, 3-cyclohexenyl and the like;
the 'heterocyclylalkyl' group used either alone or in combination with other radicals, is selected from groups containing an heterocyclyl radicals i.e suitable aromatic or non-aromatic radicals containing one or more heteroatoms such as N, O, S;
the 'cycloalkanylalkyl' group used either alone or in combination with other radicals, is selected from the groups containing a cycloalkyl radical, as define above,
the 'heteroarylalkyl' group used either alone or in combination with other radicals is selected from groups containing an heteroaryl radicals i.e. single or fused mono or bicyclic or tricyclic aromatic rings containing one or more hetero atoms selected from N, O, S.
The above and other objects of the present invention are attained as described herein below. In an embodiment, the objects are attained by the improved process for the preparation of quinolone based compounds of the formula (I) and intermediates thereof as described herein.

In embodiment, there is provided a process for the preparation of compound of formula (I):

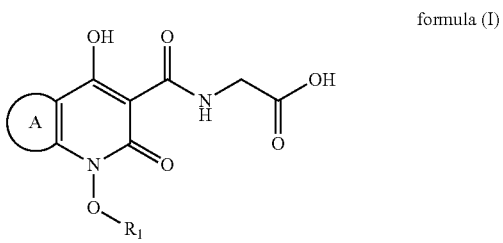

formula (I)

Wherein A is an optionally substituted aryl ring.
R$_1$ represents hydrogen, optionally substituted (C$_1$-C$_{10}$) alkyl, (C$_3$-C$_8$)cycloalkyl, (C$_5$-C$_8$)cycloalkenyl, aryl, cycloalkanylalkyl, heteroaralkyl, heterocyclylalkyl groups.
The process is for preparation of compound of formula (I) is described in details herein below (Scheme 3):

Step 1

Step 1 is divided in four parts:
Part A: The compound (VII) reacts with 2-hydroxyisoindoline-1,3-dione to give compound (VIII);
PART B: Compound (VIII) is further reacted with hydrazine hydrate to give compound (IX);
PART C: Compound (IX) is reacted with Boc.-anhydride to synthesize Boc.-protected compound which is in situ used in part D;
PART D: The product obtained in Part C is further reacted with imidazole to remove excess Boc.-anhydride to give compound (X).
Step 1': Step 1' comprises reaction of compound (XI-1) with suitable reagent to give compound (XI).
Step 2: Compound (X) and (XI) react together in presence of suitable reagents and solvents to give compound (XII).
Step 3: Compound (XII) is further deprotected in presence of suitable reagents to give compound (XIII).
Step 4: Compound (XIII) is reacted with ethyl hydrogen malonate to give compound (XIV).
Step 5: Compound (XIV) is further reacted with suitable reagents in presence of suitable solvents to give compound (XV).
Step 6: Compound (XV) is reacted with HCl salt of Glycine ethyl ester to give compound (XVI).
Step 7: Compound (XVI) is reacted with suitable acid when it get's hydrolyzed and form compound of formula (I).
In a further embodiment is provided an improved process for the preparation of compound of formula (I) as described in Scheme 3:

Scheme 3

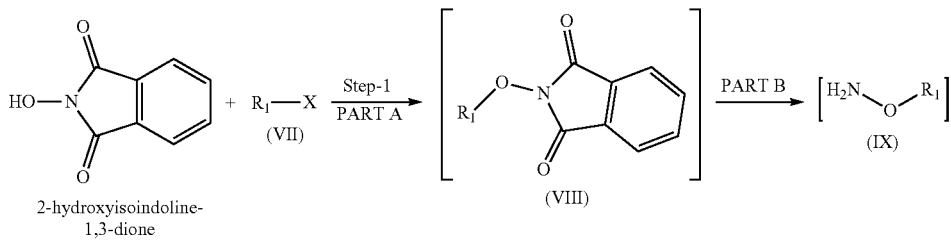

2-hydroxyisoindoline-1,3-dione

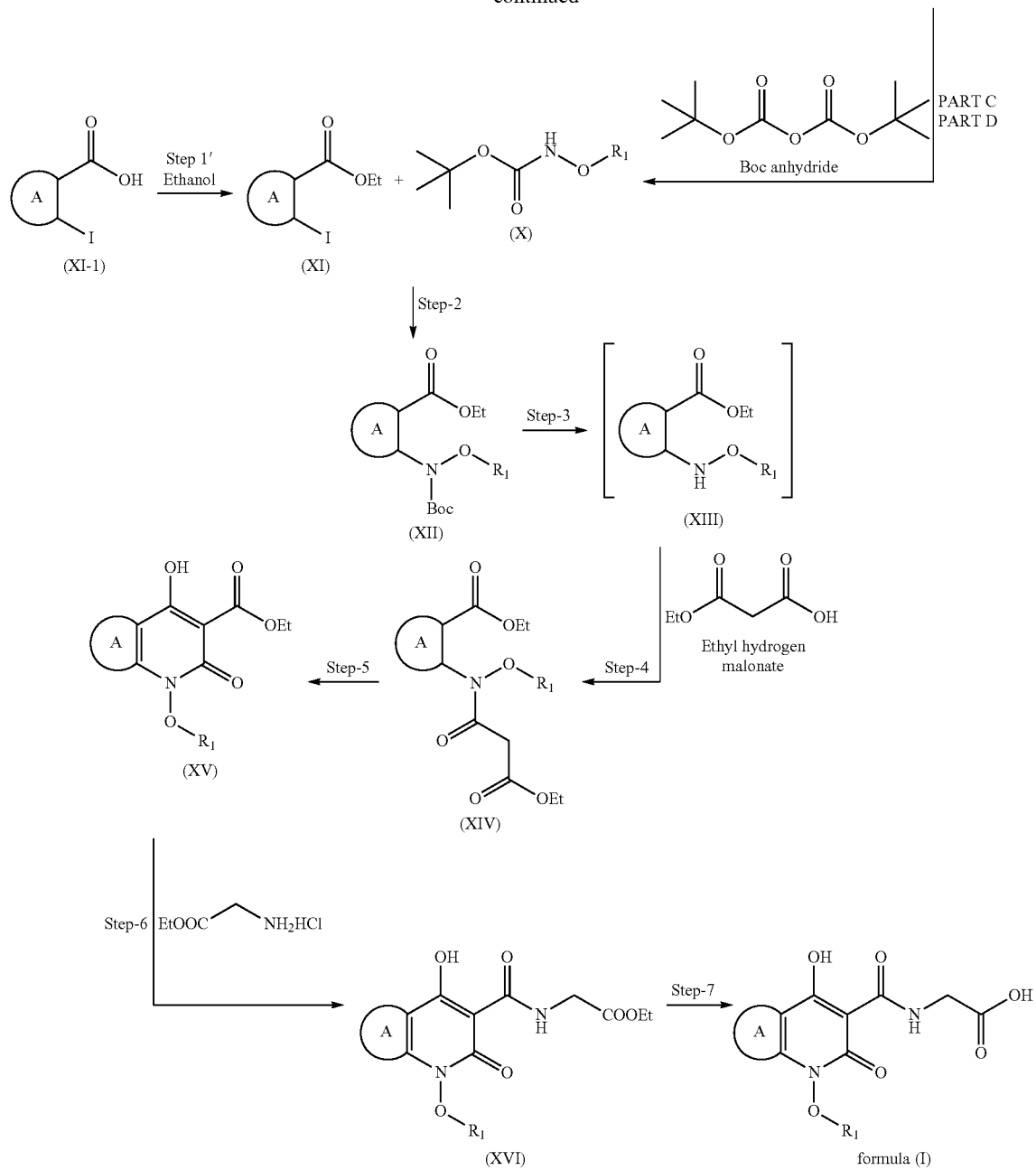

The process comprises,

Step-1 Preparation of Compound of Formula (X)

Step 1 is carried out in four parts as described below:

Part A: Preparation of Compound of Formula (VIII)

Reacting 2-hydroxyisoindoline-1,3-dione with compound (VII) in presence of suitable base and suitable solvents at temperature 0° C. to 60° C. to obtain solid product i.e. compound (VIII), which is to be used in the next (part-B) reaction, without any further purification.

Suitable base used in part A is selected from Sodium carbonate, sodium hydride, potassium hydroxide, sodium hydroxide and the like; organic bases selected from triethyl amine, N,N-diisopropyl ethyl amine, DBU, DBN, DABCO and the like.

Suitable solvent used in part A is selected from DMSO, DMF, toluene, THF, ether and the like.

Part B: Preparation of Compound of Formula (IX)

Compound (VIII) in suitable solvent is cooled to suitable temperature which further on reaction with suitable reagent in appropriate solvent gives compound of formula (IX).

Suitable solvent used in part B is selected from DCM, methanol, ethanol, toluene, THF and the like.

Suitable reagent used is selected from hydrazine hydrate, methyl hydrazine, ammonia and the like.

Suitable solvent used in part B is DCM, ethyl acetate, acetonitrile, THF, water and mixture thereof.

Part C and D: Preparation of Compound of Formula (X)

Part C

Organic layer obtained from part B (IX), was cooled to 0 to 5° C. Suitable base was added at 0 to 5° C. Boc.-anhydride is then added and reaction mixture stirred for 1 hour at 0 to 5° C. and further stirred for 18 hrs at 20 to 35° C. to obtain compound (X).

Suitable base used in Part C is sodium carbonate, potassium carbonate, triethyl amine, N,N-diisoppropyl ethyl amine, DBU, DBN, DABCO and the like.

Suitable solvent used in step C is DCM, ethyl acetate, acetonitrile, THF and the like and mixture thereof.

Part D

Imidazole is added to compound of formula (X) obtained from part-C, the reaction mixture was stirred at 20 to 35° C. for 20 hours to remove excess Boc.-anhydride and obtain compound (X).

Step-1' Preparation of Compound of Formula (XI)

Compound (XI-1) was reacted with ethanol and sulfuric acid. Reaction mixture was stirred at 80 to 85° C. and stirred for 20 hours to obtain compound (XI).

Step-2 Preparation of Compound of Formula (XII)

Reacting compound (X) and (XI) in presence of Copper (I) iodide, glycine as a ligand with suitable solvent and suitable base at suitable temperature to give compound (XII).

The suitable solvent used for dissolving the compound (X) and (XI) is selected from toluene, DMF, 1,4-dioxane, DME and the like.

Suitable base used is selected form Potassium carbonate or any other suitable base $Cs_2CO_3$, NaOtBu, $K_3PO_4$ and the like.

Other suitable solvent which may be used is selected from ethanol, methanol, isopropyl alcohol, butanol and the like.

Other suitable ligand used is selected from 1,10-phenanthroline, proline.

Suitable temperature for reflux is 78 to 85° C.

Step-3 Preparation of Compound of Formula (XIII)

Compound (XII) further is dissolved in suitable solvent and cooled externally. To this alcoholic solution of acid was added drop wise. Further reaction mixture was stirred for 3 hours to get compound (XIII). Suitable alcoholic solution of acid is selected from methanolic HCl, isopropyl HCl, ethanolic HCl, p-toluene sulphonic acid solution and the like.

Step-4 Preparation of Compound of Formula (XIV)

Compound (XIV) after dissolving in suitable solvent, is reacted with suitable base and Phosphorous oxychloride to obtain compound (XIV) as an oily product.

Suitable solvent used herein is selected from acetonitrile, DCM, toluene and the like.

Suitable base used is selected form pyridine, triethyl amine, N,N-diisopropyl amine and the like.

Step-5 Preparation of Compound of Formula (XV)

Compound (XIV) is further dissolved in suitable solvent and reacted with suitable reagent at 10 to 20° C. After completion of reaction; reaction mass was acidified with suitable acid solution to obtain compound (XV). Compound (XV) was further purified with suitable solvent.

Suitable reagent used in this step is selected from sodium methoxide, sodium ethoxide and the like.

Suitable acid solution used herein is selected from aqueous hydrochloric acid, citric acid, acetic acid, sulphuric acid and the like.

Suitable solvent used for reaction as well as purification herein is selected form methanol and ethanol DMF, methanol, ethanol, DMSO and the like.

Step-6 Preparation of Compound (XVI)

After dissolving compound (XV) in suitable solvent, it is further reacted with glycine ethyl ester HCl in presence of suitable base to obtain compound (XVI). It was further purified with suitable solvent.

Suitable solvent used is selected from tetrahydrofuran, 1, 4-dioxane, acetonitrile, ethyl acetate, toluene and the like.

Suitable solvent for purification used is selected form methanol, ethanol, THF and the like.

Suitable base is selected from N, N-diisopropylethyl amine, triethyl amine and the like.

Step-7 Preparation of Compound of Formula (I)

Compound (XVI) is dissolved in suitable solvent to undergo hydrolysis in presence of suitable aqueous base. Reaction mass was acidified with suitable acid after the completion of reaction to obtain compound of formula (I).

Suitable solvent used is selected form methanol, ethanol, THF, isopropyl alcohol and the like.

Aqueous solution of suitable base is selected from sodium hydroxide, lithium hydroxide, potassium hydroxide and the like.

Suitable acid solution used herein is selected from HCl, citric acid, acetic acid, sulphuric acid and the like.

In another embodiment, process for the preparation of compound of formula (I-a) is described.

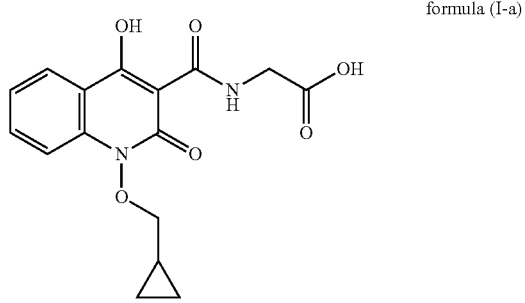 [SMILES: O=C(O)CNC(=O)c1c(O)c2ccccc2n(OCC2CC2)c1=O]

formula (I-a)

The process comprises the following steps (scheme 4):

Step 1a

Step 1a is divided into four parts:
Part A': The compound (VII-a) reacts with 2-hydroxyisoindoline-1,3-dione to give compound (VIII-a);

PART B': Compound (VIII-a) is further reacted with hydrazine hydrate to give compound (IX-a);

PART C': Compound (IX-a) is reacted with Boc.-anhydride to obtain Boc.-protected compound which is in situ used in part D;

PART D': Product of step C is further reacted with imidazole to remove excess reagent to give compound (X-a).

Step 1': Step 1' comprised reaction of compound (XI-1 a) with suitable reagent to give compound (XI-a).

Step 2': Compound (X-a) and (XI-a) react together in presence of suitable reagents and solvents to give compound (XII-a).

Step 3': Compound (XII-a) is further deprotected in presence of suitable reagents to give compound (XIII-a).

Step 4': Compound (XIII-a) is reacted with ethyl hydrogen malonate to give compound (XIV-a).

Step 5': Compound (XIV-a) is further reacted with suitable reagents in presence of suitable solvents to give compound (XV-a).

Step 6': Compound (XV-a) is reacted with HCl salt of Glycine ethyl ester to give compound (XVI-a).

Step 7': Compound (XVI-a) is reacted with suitable acid to get hydrolysed and form compound for formula (I-a).

In yet another preferred embodiment, the invention provides an improved process for the preparation of compound of formula (I-a) as described in Scheme 4.

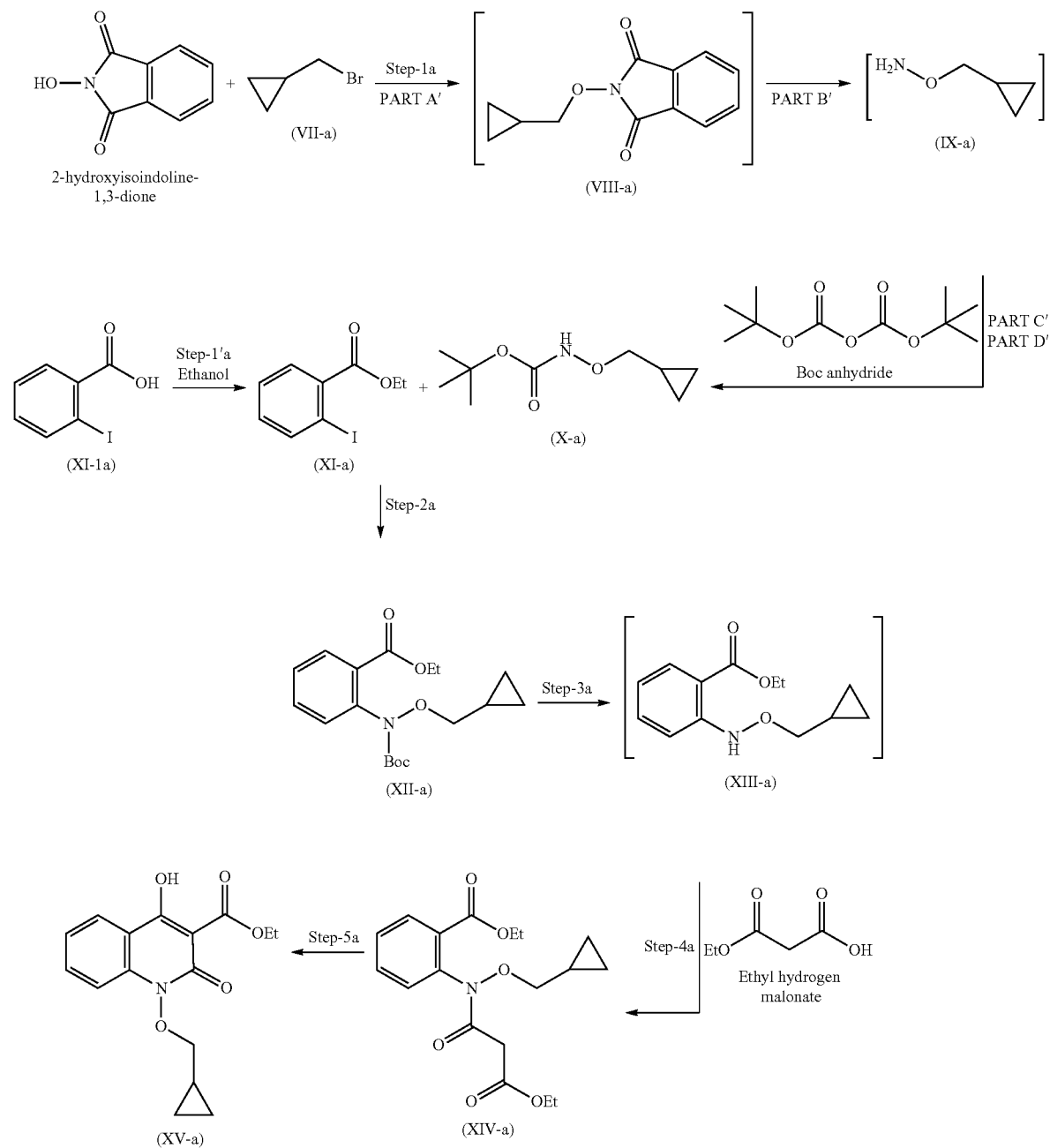

Scheme 4

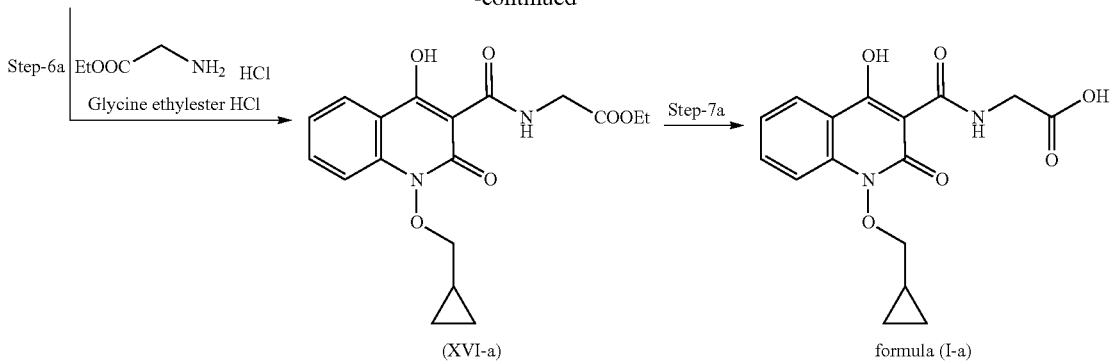

The process for the preparation of compound of formula (I-a) comprises the following steps:

Step-1' Preparation of Compound (X-a)

Step 1 was carried out in four parts as described below:

Part A': Preparation of Compound (VIII-a)

Reacting 2-hydroxyisoindoline-1,3-dione with compound (VII-a) in presence of suitable base and suitable solvents at temperature 0° C. to 60° C. to obtain solid product i.e. compound (VIII-a), which is to be used in the next (Part-B) reaction, without any further purification.

Suitable base used in part A is selected from sodium carbonate, sodium hydride, potassium hydroxide, sodium hydroxide and the like, organic bases is selected from triethyl amine, N,N-diisopropyl ethyl amine, DBU, DBN, DABCO and the like.

Suitable solvent used in part A is selected from DMSO, DMF, toluene, THF, ether and the like.

Part B': Preparation of Compound (IX-a)

Reaction of compound (VIII-a) with suitable reagent such as from hydrazine hydrate, Methyl hydrazine, ammonia in suitable solvent at suitable temperature to, gives compound of formula (IX-a).

Suitable solvent used in part B' is selected from DCM, methanol, ethanol, toluene, THF and the like.

Suitable temperature used for addition of reagent is 0 to 10° C.

Part C' and PART D': Preparation of Compound (X-a)

Part C'

Organic layer obtained from part-B' (IX-a), was cool to 0 to 5° C. Suitable base was added at 0 to 5°C. Boc. anhydride is to be added to the reaction mixture and it was stirred for 1 hour at 0 to 5 ° C. and further stirred for 18 hrs at 20 to 35°C. to obtain compound (IX-a).

Suitable base used in Part C' is sodium carbonate, potassium carbonate, triethyl amine, N,N-tri isopropyl ethyl amine, DBU, DBN, DABCO and the like.

Suitable solvent used in step C' is DCM, ethyl acetate, acetonitrile, THF and mixture thereof.

Part D'

Imidazole is added to Compound (X-a) obtained from part-C'. Reaction mixture was stirred at 20 to 35° C. for 20 hours to remove excess Boc.-anhydride obtain compound (X-a).

Step-1'a: Preparation of Compound (XI-a)

Compound (XI-Ia) was reacted with ethanol and sulfuric acid. Reaction mixture was stirred at 80 to 85°C. and stirred for 20 hours to obtain compound (XI-a).

Step-2a Preparation of Compound (XII-a)

Reacting compound (X-a) and (XI-a) by dissolving them in suitable solvent in presence of Copper (I) iodide, and glycine as a ligand with suitable base at suitable temperature gives compound (XII-a).

Suitable solvent used for dissolving the compound (X-a) and (XI-a) is selected from toluene, DMF, 1,4-dioxane, DME and the like.

Suitable base used is selected form Potassium carbonate or any other suitable base $Cs_2CO_3$, NaOtBu, $K_3PO_4$ and the like.

Other suitable solvent used is selected from Ethanol, methanol, Isopropyl alcohol, butanol and the like.

Other suitable ligand used is selected from 1,10-phenanthroline, proline.

Suitable temperature for reflux is 78 to 85° C.

Step-3a Preparation of Compound (XIII-a)

Compound (XII-a) further is dissolved in suitable solvent and cool externally. To this alcoholic solution of acid was added drop wise. Further reaction mixture is allowed to stir for 3 hours to get compound (XIII-a).

Suitable alcoholic solution of acid is selected from methanolic HCl, isopropanolic HCl, ethanolic HCl, p-toluene sulphonic acid solution and the like.

Step-4a Preparation of Compound (XIV-a)

Compound (XIV-a) after dissolving in suitable solvent, is reacted with suitable base and phosphorous oxychloride to obtain compound (XIV-a) as an oily product.

Suitable solvent used herein is selected from acetonitrile, DCM, toluene and the like.

Suitable base used is selected form Pyridine, Triethyl amine, N,N-Diisopropyl amine and the like.

Step-5a Preparation of Compound (XV-a)

Compound (XIV-a) further is dissolved in suitable solvent and reacted with suitable reagent at 10 to 20° C. After completion of reaction, reaction mass was acidified with suitable acid solution to obtain compound (XV-a). Compound (XV-a) was further purified with suitable solvent.

Suitable reagent is selected from sodium methoxide, sodium ethoxide and the like.

Suitable acid solution used herein is selected from aqueous hydrochloric acid, citric acid, acetic acid, sulphuric acid and the like.

Suitable solvent used for reaction as well as purification herein is selected form methanol and ethanol DMF, methanol, ethanol, DMSO and the like.

Step-6a: Preparation of Compound (XVI-a)

After dissolving compound (XV-a) in suitable solvent, it is further reacted with glycine ethyl ester HCl in presence of suitable base to obtain compound (XVI-a). It was further purified with suitable solvent.

Suitable solvent used is selected from tetrahydrofuran, 1,4-dioxane, acetonitrile, ethyl acetate, toluene and the like.

Suitable solvent for purification used is selected form methanol, ethanol, THF and the like.

Suitable base is selected from N,N-Diisopropylethyl amine, triethyl amine and the like.

Step-7a: Preparation of Compound of Formula (I-a)

Compound (XVI-a) is dissolved in suitable solvent to undergo hydrolysis in presence of suitable aqueous base. Reaction mass was acidified with suitable acid after the completion of reaction to obtain compound of formula (I-a).

Suitable solvent used is selected form methanol, ethanol, THF, isopropyl alcohol and the like.

Aqueous solution of suitable base is selected from sodium hydroxide, Lithium Hydroxide, Potassium Hydroxide and the like.

Suitable acid solution use herein is selected from HCl, citric acid, acetic acid, sulphuric acid and the like.

In another embodiment is provided a compound (XII-a).

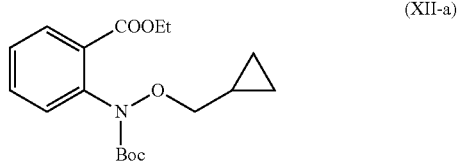 [SMILES: CCOC(=O)c1ccccc1N(OCC1CC1)C(=O)OC(C)(C)C]

In yet another embodiment is provided a process for the preparation of compound (XII-a) as describe in scheme 5.

Scheme 5

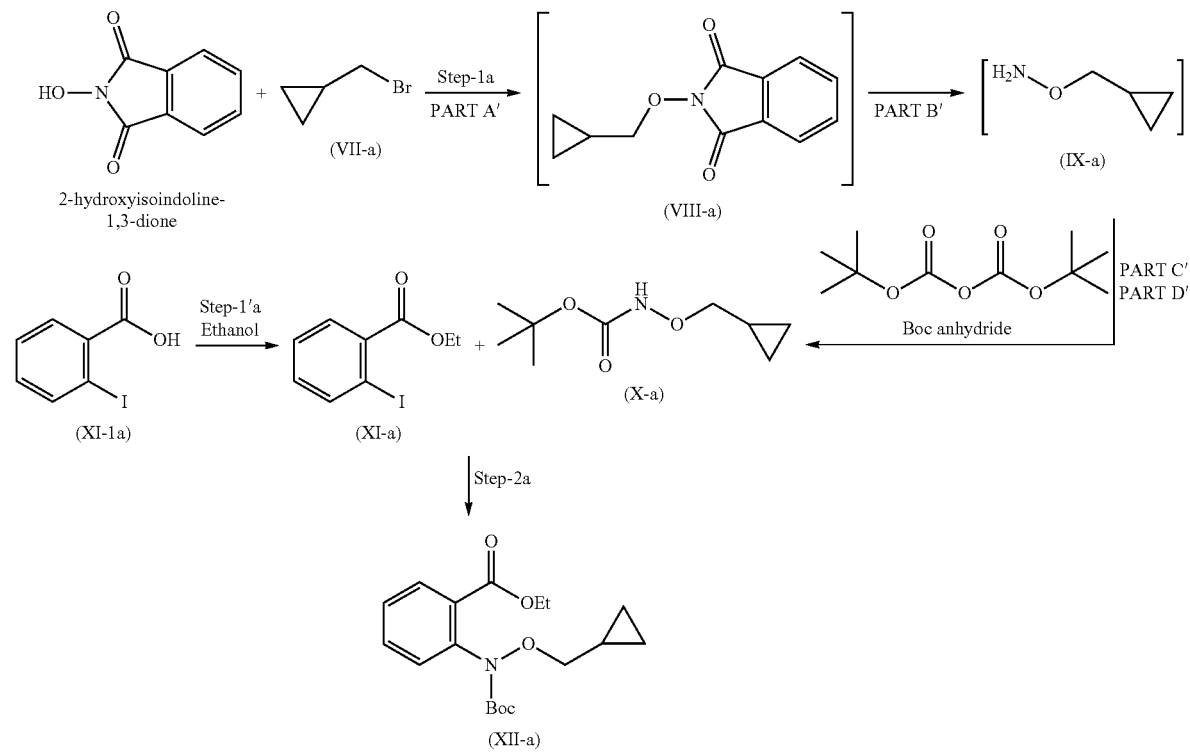

The process for the preparation of compound of formula (I-a) comprises, the following steps:

Step-1' Preparation of Compound (X-a)

Step 1 was carried out in four parts as described below:

Part A': Preparation of Compound (VIII-a)

Reacting 2-hydroxyisoindoline-1,3-dione with compound (VII-a) in presence of suitable base and suitable solvents at temperature 0° C. to 60° C. to obtain solid product i.e. compound (VIII-a), which is to be used in the next (Part-B) reaction, without any further purification.

Suitable base used in part A is selected from sodium carbonate, sodium hydride, potassium hydroxide, sodium hydroxide and the like, organic bases is selected from triethyl amine, N,N-diisopropyl ethyl amine, DBU, DBN, DABCO and the like.

Suitable solvent used in part A is selected from DMSO, DMF, toluene, THF, ether and the like.

Part B': Preparation of Compound (IX-a)

Reaction of compound (VIII-a) with suitable reagent such as from hydrazine hydrate, Methyl hydrazine, ammonia in suitable solvent at suitable temperature to, gives compound of formula (IX-a).

Suitable solvent used in part B' is selected from DCM, methanol, ethanol, toluene, THF and the like.

Suitable temperature used for addition of reagent is 0 to 10° C.

Part C' and PART D': Preparation of Compound (X-a)

Part C'

Organic layer obtained from part-B' (IX-a), was cool to 0 to 5° C. Suitable base was added at 0 to 5° C. Boc. anhydride is to be added and reaction mixture and stirred for 1 hour at 0 to 5° C. and further stirred for 18 hrs at 20 to 35° C. to obtain compound (IX-a).

Suitable base used in Part C' is sodium carbonate, potassium carbonate, triethyl amine, N,N-tri isopropyl ethyl amine, DBU, DBN, DABCO and the like.

Suitable solvent used in step C' is DCM, ethyl acetate, acetonitrile, THF and mixture thereof.

Part D'

Imidazole is added to Compound (X-a) obtained from part-C'. Reaction mixture was stirred at 20 to 35° C. for 20 hours to remove excess Boc.-anhydride obtain compound (X-a).

Step-1'a: Preparation of Compound (XI-a)

Compound (XI-1a) was reacted with ethanol and sulfuric acid. Reaction mixture was stirred at 80 to 85° C. and stirred for 20 hours to obtain compound (XI-a).

Step-2a Preparation of Compound (XII-a)

Reacting compound (X-a) and (XI-a) by dissolving them in suitable solvent in presence of Copper (I) iodide, and glycine with suitable base at suitable temperature gives compound (XII-a). Suitable solvent used for dissolving the compound (X-a) and (XI-a) is selected from toluene, DMF, 1,4-dioxane, DME and the like.

Suitable base used is selected form Potassium carbonate or any other suitable base $Cs_2CO_3$, NaOtBu, $K_3PO_4$ and the like.

Other suitable solvent used is selected from Ethanol, methanol, Isopropyl alcohol, butanol and the like.

Suitable temperature for reflux is 78 to 85° C.

In another embodiment is provided a use of intermediate compound (XII-a) for the preparation of compound of formula (I-a).

In a further embodiment of the invention disclosed a crystalline Form of the compound of formula (I-a).

In another embodiment the crystalline Form of the compound of formula (I-a) has a powder X-ray diffraction pattern as given in FIG. 1;

In yet another embodiment the crystalline Form of the compound of formula (I-a) has a powder X-ray diffraction pattern having a peak at about 8.9±0.2 degrees 2-theta;

In yet another embodiment the crystalline Form of the compound of formula (I-a) has a powder X-ray diffraction pattern having additional peaks at about 8.0°±0.2, 10.6±0.2, 11.3±0.2, 16.1±0.2, 25.5±0.2, 26.4±0.2 degrees 2-theta.

In order to obtain marketing approval for a new drug product, manufacturers must submit the evidence to the regulatory authority that the product is acceptable for administration to humans. Such a submission must include impurity profile of the product to demonstrate that the impurities are either absent, or present in a negligible amount. Different regulatory authorities have promulgated guidelines requiring applicants to identify the impurities present in the product and also disclose their concentration in the product. They also provide the maximum level of impurities allowable in the product. Thus for e.g. USFDA recommends that drug applicants identify all the impurities having concentration of 0.1% or greater, in the active ingredient. Therefore, there is a need to check impurity profile and identify the impurities and also their concentration in the active ingredient.

Following novel compounds (XVII to XIX) were also obtained during the synthesis of the compound of formula (I-a). These compounds may be generated as generates during process for the preparation of compound of formula (I-a).

The present invention thus provides following a new impurities of compound of formula (Ia):
  i. Compound XVII having chemical name 2-(2-(1-(cyclopropylmethoxy)-4-hydroxy-2-oxo-1,2-dihydroquinoline-3-carboxamido)acetamido)acetic acid (XVII), and having the following chemical structure:

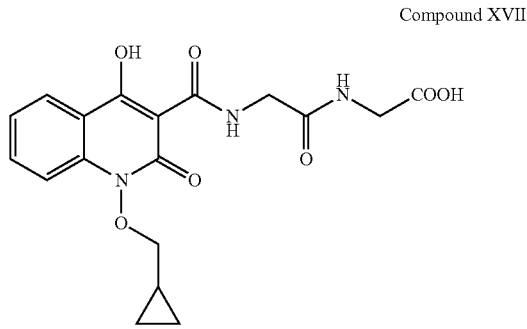 [SMILES: O=C(O)CNC(=O)CNC(=O)c1c(O)c2ccccc2n(OCC2CC2)c1=O]

Compound XVII

In an embodiment the compound of formula (XVII) is controlled in formula (I-a) with the limit of 0.01% to 2.0% preferably not more than 0.20%.

ii. Compound XVIII having chemical name (1-(cyclopropylmethyl)-4-hydroxy-2-oxo-1,2-dihydroquinoline-3-carbonyl)glycine(XVIII), and which has the following chemical structure:

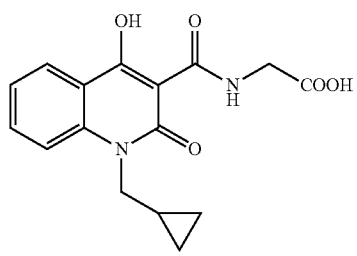

Compound XVIII

In an embodiment the compound of formula (XVIII) is controlled in formula (I-a) with the limit of 0.01% to 2.0% preferably not more than 0.30%.

iii. Compound XIX having chemical name (1-butoxy-4-hydroxy-2-oxo-1,2-dihydroquinoline-3-carbonyl)glycine, and has the following chemical structure:

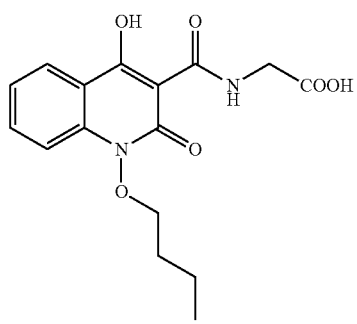

Compound XIX

In an embodiment the compound of formula (XVIII) is controlled in formula (I-a) with the limit of 0.01% to 2.0% preferably not more than 0.15%.

Present invention also discloses that compounds of formula (XX) and (XXI) are also generated during the process of the preparation of compound (I-a).

iv. Compound XX having chemical name (4-hydroxy-2-oxo-1,2-dihydroquinoline-3-carbonyl)glycine and has following chemical structure:

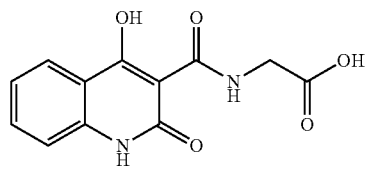

Compound XX v. Compound XX having chemical name ethyl 1-(cyclopropylmethoxy)-4-hydroxy-2-oxo-1,2-dihydroquinoline-3-carboxylate and has following structure:

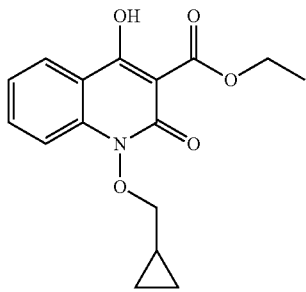

Compound XXI

In one of the aspect of the invention, there is provided processes for the preparation of compounds (XVII), (XVIII), (XIX), (XX) and (XXI).

Preparation of Compound (XVII)

Compound of the formula (XVII) can be prepared as described in scheme 6.

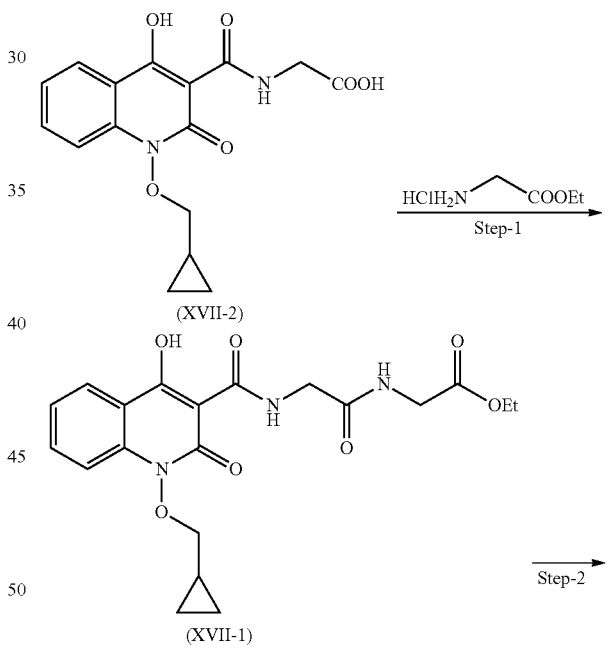

Scheme 6

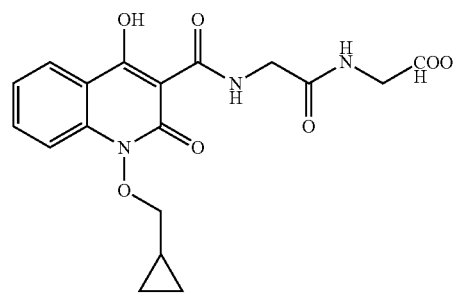

(XVII)

Step 1. Preparation of Compound (XVII-1)

Compound (XVII-2) and ethyl glycinate hydrochloride reacts in presence of suitable base and solvent to give compound of formula (XVII-1).
Suitable solvent is selected from DMA, THF, ACN and the like.
Suitable base is TEA.

Step 2. Preparation of Compound (XVII)

Compound (XVII-1) is further reacted with methanol and water to give hydrolyzed product of formula (XVII).

Preparation of Compound (XVIII)

Compound of the formula (XVIII) can be prepared as described in scheme 7.

Step 2. Preparation of Compound (XVIII-5)

Compound of formula (XVIII-6) get reduced in presence of suitable reagent and solvent to give compound (XVIII-5).
Suitable reagent is stannous chloride dehydrate.
Suitable solvent is selected from methanol, tetrahydrofuran and the like.

Step 3. Preparation of Compound (XVIII-4)

Compound of formula (XVIII-5) reacts with Iodomethyl cyclopropane in presence of suitable base and solvent to give compound of formula (XVIII-4).
Suitable base is selected from cesium carbonate, potassium carbonate, sodium carbonate, etc.

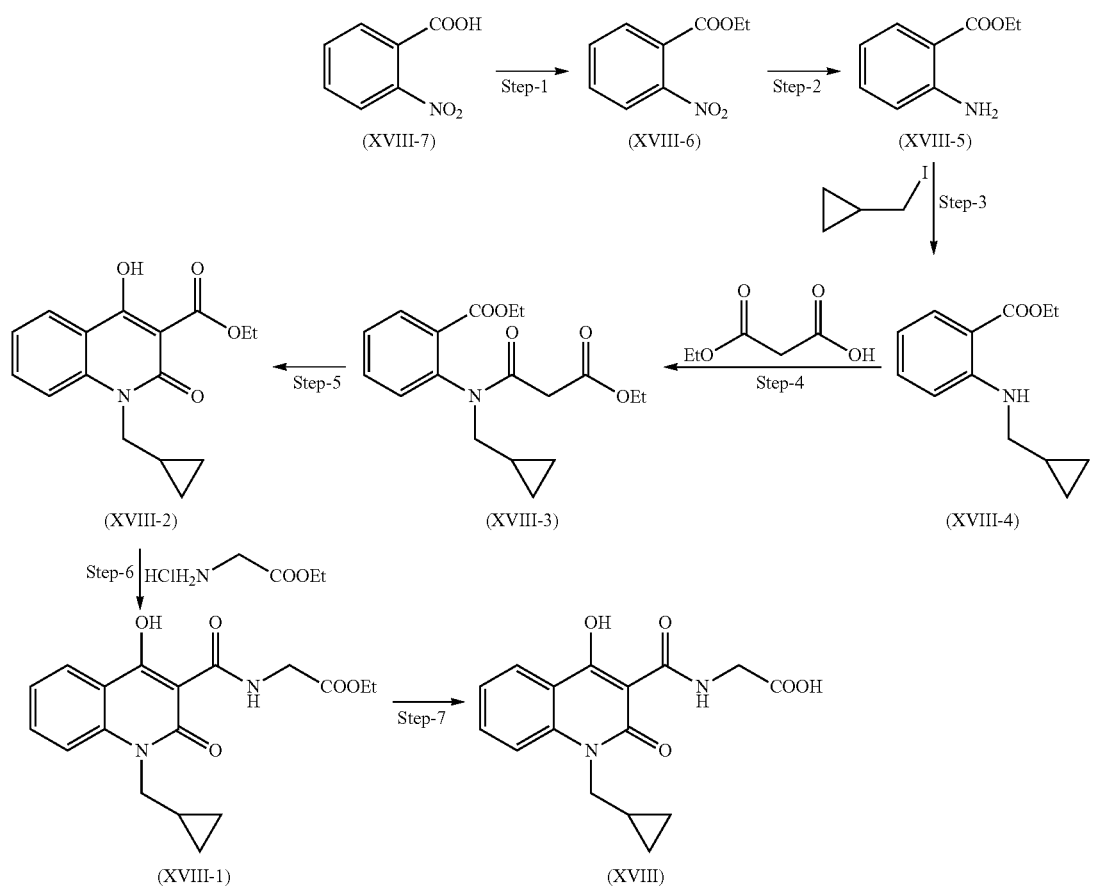

Scheme 7

Step 1. Preparation of Compound (XVIII-6)

Reacting compound (XVIII-7) with diethyl sulfate in presence of suitable solvent and base to get compound of formula (XVIII-6).
Suitable temperature for the reaction is 55 to 60° C.
Suitable solvent is acetone and base is selected from sodium bicarbonate, potassium bicarbonate, Sodium carbonate, sodium carbonate, and the like.

Suitable solvent is selected from DMF, DMSO, ACN and the like.
Suitable temperature range is 10 to 15° C.

Step 4. Preparation of Compound (XVIII-3)

Compound (XVIII-4) reacts with 3-ethoxy-3-oxopropanoic acid in presence of other suitable reagent, suitable base and suitable solvent to give compound (XVIII-3)
Suitable reagent is POCl₃
Suitable base is selected from pyridine, triethyl amine, etc.

Suitable solvent is selected form acetonitrile, DMF, DMSO, and the like.

Step 5. Preparation of Compound (XVIII-2)

Compound of formula (XVIII-3) gets cyclized in presence of suitable base and solvent to give compound of formula (XVIII-2)

Suitable base is selected from sodium methoxide, sodium ethoxide, etc.

Suitable solvent is selected from methanol, ethanol, isopropyl alcohol and the like.

Step 6. Preparation of Compound (XVIII-1)

Compound of formula (XVIII-2) dissolved in suitable solvent and reacted with glycine diethyl ester hydrochloride and suitable base to get compound of formula (XVIII-1).

Suitable solvent is selected from 1,4-dioxane, tetrahydrofuran and mixture thereof.

Suitable base is selected from Di isopropylethyl amine, and the like.

Step 7. Preparation of Compound (XVIII)

On reacting compound of formula (XVIII-1) with methanol and water in presence of suitable base at room temperature and subsequent acidification of the hydrolyzed compound gives compound of formula (XVIII).

Suitable base is selected from sodium hydroxide, potassium hydroxide, etc.

Preparation of Compound (XIX)

Compound of the formula (XIX) can be prepared as described in scheme 8.

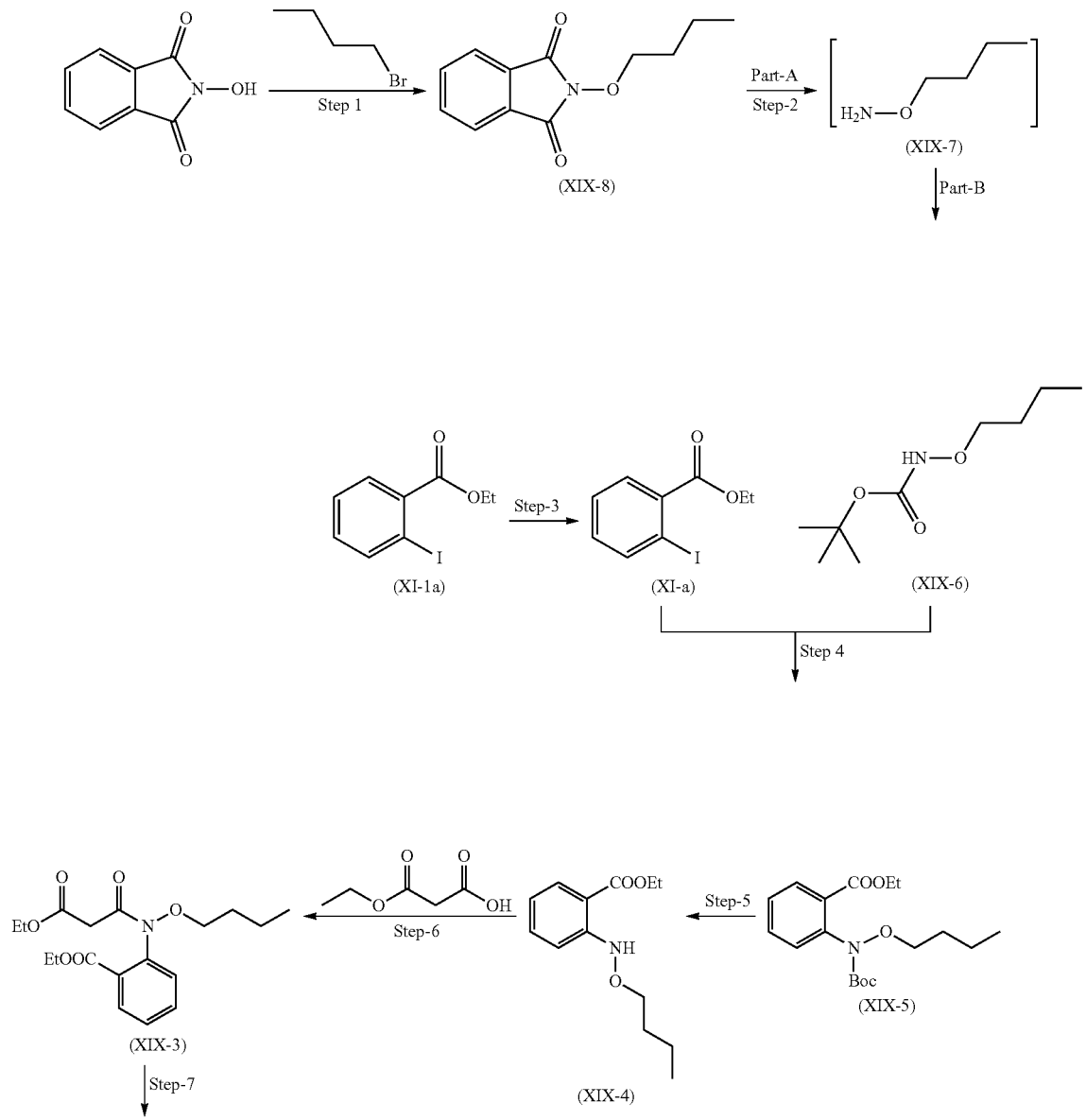

Scheme 8

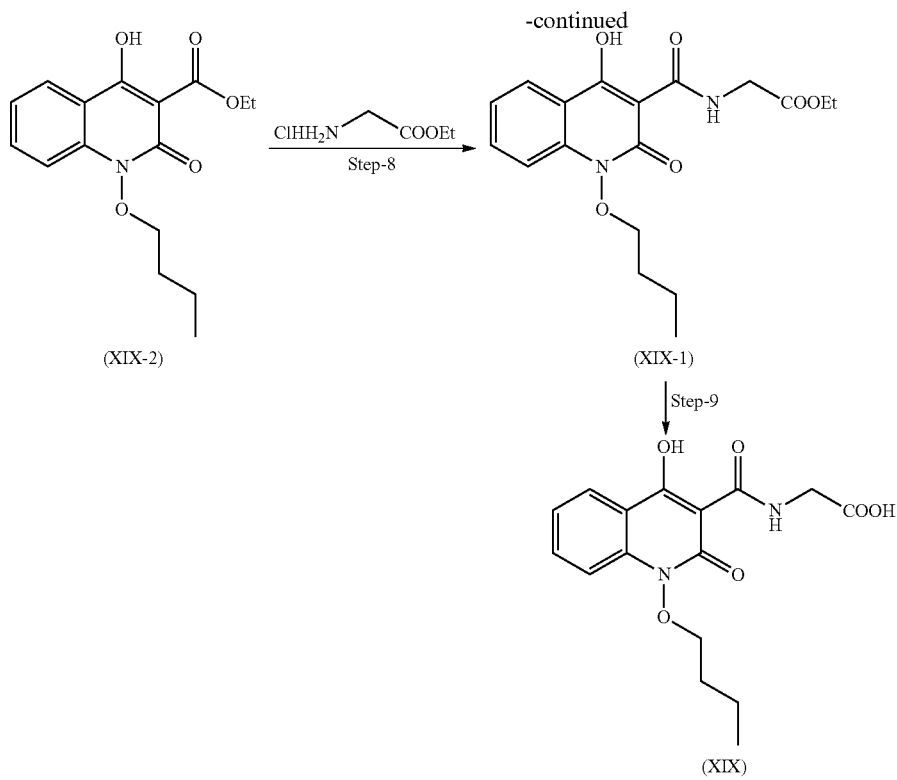

Step 1. Preparation of Compound (XIX-8)

Reacting 2-hydroxyisoindoline-1,3-dione with 1-Bromobutane in presence suitable base and solvent and the mixture was stirred at 40-50° C. to get the compound (XIX-8)

Suitable base is selected from sodium carbonate, sodium hydroxide, potassium carbonate, potassium hydroxide and the like.

Suitable solvent is selected from DMSO, DMF, acetonitrile and the like.

Step 2. Preparation of Compound (XIX-6)

Step 2 is further divided in two parts A and B.
Part A: compound (XIX-8) reacts with hydrazine hydrate with cooling to get compound (XIX-7).
Part B: Compound (XIX-7) further reacts with Di-tert-butyl-dicarbonate to get compound (XIX-6)
Suitable solvents used for both part A and B are selected from dichloromethane, methanol and the like.

Step 3. Preparation of Compound (XI-a)

Compound (XI-1a) was reacted with ethanol and sulfuric acid. Reaction mixture was stirred at 80 to 85° C. and stirred for 20 hours to obtain compound (XI-a).

Step 4. Preparation of Compound (XIX-5)

Compound (XI-a) and (XIX-6) react together in presence of copper iodide in presence of suitable base and suitable solvent.
Suitable solvent used for dissolving the compounds is selected from toluene, DMF, 1,4-dioxane, DME and the like.

Suitable base used is selected form Potassium carbonate or any other suitable base $Cs_2CO_3$, NaOtBu, $K_3PO_4$ and the like.
Other suitable solvent which can be used is selected from Ethanol, methnol, isopropyl alcohol, butanol and the like.
Suitable temperature for reflux is 78 to 85° C.

Step 5. Preparation of Compound (XIX-4)

Compound (XIX-5) is further de-protected in presence of alcoholic acid solution to yield compound (XIX-4).
Suitable alcoholic solution of acid is selected from methanolic HCl, isopropanolic HCl, ethanolic HCl, p-toluene sulphonic acid solution and the like.

Step 6. Preparation of Compound (XIX-3)

Compound (XIX-4) after dissolving in suitable solvent, is reacted with suitable base and phosphorous oxychloride to obtain compound (XIX-3) as liquid product.
Suitable solvent used herein is selected from acetonitrile, DCM, toluene and the like.
Suitable base used is selected form Pyridine, Triethyl amine, N,N-Diisopropyl amine and the like.

Step 7. Preparation of Compound (XIX-2)

Compound (XIX-3) further is dissolved in suitable solvent and reacted with suitable reagent at 10 to 20° C. After completion of reaction, reaction mass was acidified with suitable acid solution to obtain compound (XIX-2). Compound (XIX-2) was further purified with suitable solvent.
Suitable reagent may be selected from sodium methoxide, sodium ethoxide and the like.
Suitable acid solution used herein is selected from aqueous hydrochloric acid, citric acid, acetic acid, sulphuric acid and the like.

Suitable solvent used for reaction as well as purification herein is selected form methanol and ethanol DMF, methanol, ethanol, DMSO and the like.

Step 8. Preparation of Compound (XIX-1)

After dissolving compound (XIX-2) in suitable solvent, it is further reacted with glycine ethyl ester HCl in presence of suitable base to obtain compound (XIX-1). It was further purified with suitable solvent.

Suitable solvent used is selected from tetrahydrofuran, 1, 4-dioxane, acetonitrile, ethyl acetate, toluene and the like.

Suitable solvent for purification used is selected form methanol, ethanol, THF and the like.

Suitable base is selected from N, N-diisopropylethyl amine, triethyl amine and the like.

Step 9. Preparation of Compound (XIX)

Compound (XIX-1) is dissolved in suitable solvent to undergo hydrolysis in presence of suitable aqueous base. Reaction mass was acidified with suitable acid after the completion of reaction to obtain compound of formula (XIX).

Suitable solvent used is selected form methanol, ethanol, THF, isopropyl alcohol and the like.

Aqueous solution of suitable base is selected from sodium hydroxide, Lithium Hydroxide, Potassium Hydroxide and the like.

Suitable acid solution use herein is selected from HCl, citric acid, acetic acid, sulphuric acid and the like.

The invention is further exemplified by the following examples which represent some of the preferred mode of carrying out the invention and should not be construed to be limiting the scope of the invention as described herein in any way.

Example 1 Preparation of (1-(cyclopropylmethoxy)-4-hydroxy-2-oxo-1,2-dihydroquinoline-3-carbonyl) glycine

Step 1 Preparation of tert-butyl (cyclopropylmethoxy)carbamate (X-a)

Process for the preparation of tert-butyl (cyclopropylmethoxy)carbamate is further divided in four steps (i.e. Step A', B', C' and D')

Part-A: Process for Preparation of 2-(cyclopropylmethoxy)isoindoline-1,3-dione (VIII-a):

In a 5 L fixed glass assembly, DMSO (1.0 L) was charged at room temperature. N-hydroxyphthalimide (200 g, 1.226 mol) was added in one lot at room temperature. Potassium carbonate (271 g, 1.961 mol) was added carefully at room temperature. After complete addition of potassium carbonate, reaction mixture turned out to thick slurry. Cyclopropyl methyl bromide (198.7 g, 1.471 mol) was added carefully at room temperature. Reaction mixture was stirred for 3 hrs at 45 to 55° C. Reaction mixtures cooled to room temperature and dump the reaction mass in to cold water (5.0 L). The reaction mixture was then charged with ethyl acetate (2.0 L). After complete addition of ethyl acetate, reaction mixture turns out to be clear solution. At room temperature it was stirred for 30 minutes and the organic layer was separated. Aqueous layer was again extracted twice with ethyl acetate (1×2.0 L) and (1×1.0 L). Combined ethyl acetate layer then wash twice with water (2×1.0 L) and 20% brine solution (1.0 L) and separated aqueous layer. Ethyl acetate was concentrated in vacuo to get solid product, which used in the next (Part-B) reaction, without any further purification.

Part-B: Process for Preparation of O-(cyclopropylmethyl)hydroxylamine (IX-a):

DCM (2.0 L) was added in to solid product obtained in part-A at room temperature. The reaction mixture was cooled down to 0 to 10° C. Hydrazine hydrate (117.9 g, 2.353 mol) was added carefully at 0 to 10° C. After complete addition of hydrazine hydrate the reaction mixture turned to thick slurry. Reaction mixture was stirred for 18 hrs at 20 to 35° C. Solid organic material was filtered off through hyflow supercel bed. Organic solid impurity was removed by washing with DCM twice, combined all filtrate again wash with twice water and separated aqueous layer. Organic layer washed with 20% sodium chloride solution (0.8 L) and separated aqueous layer. Organic layer was used in next (Part-C) reaction without any further purification.

Part-C and Part D: Process for the Preparation of tert-butyl (cyclopropylmethoxy)carbamate (X-a)

Part-C

Organic layer obtained from part-B cool to 0 to 5° C. Sodium carbonate (249.5 g, 2.353 mol) added at 0 to 5° C.

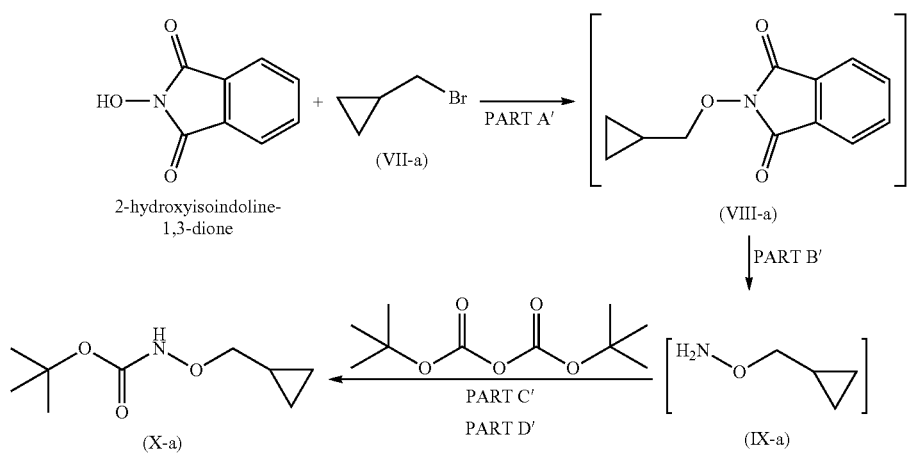

Boc anhydride (205.5g, 0.944 mol) was added carefully at 0 to 5° C. Upon completion of addition of Boc anhydride the reaction mass turn to be thick slurry. Stir reaction mixture for 1 hour at 0 to 5° C. Cooling was removed and reaction mixture was stirred for 18 hrs at 20 to 35° C.

Inorganic solid further filtered off and wash with twice DCM (2×0.2 L). Combined filtrate, which was used in next (Part-D) reaction, without any further purification.

Part-D

Organic layer obtained from part-C and imidazole (64.1 g, 0.944 mol) were mixed carefully at 20 to 35° C. Reaction mixture was stirred for 20 hours at 20 to 35° C. Reaction mixture then washed with thrice aqueous hydrochloric acid solution in water and separated aqueous layer. Organic layer was then washed with water and 20% brine solution and separated aqueous layer. DCM was concentrated in vacuo to get tert-butyl (cyclopropylmethoxy)carbamate in 68% yield, as an oil, which was used in next the reaction, without any further purification. HPLC Purity: 97.89%

Step 1'a Process for Preparation of ethyl 2-iodobenzoate (XI-a)

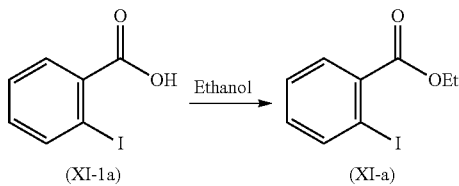 [SMILES: O=C(O)c1ccccc1I ; CCOC(=O)c1ccccc1I]

In a 5 L fixed glass assembly, Ethanol (1.25 L) charged at room temperature. 2-iodobenzoic acid (250 g, 1.00 mol) was added in one lot at room temperature. Sulphuric acid (197.7 g, 2.01 mol) was added carefully in to reaction mixture at 20 to 35° C. The reaction mixture was heated to 80 to 85° C. Reaction mixture was stirred for 20 hours at 80 to 85° C. After completion of reaction distilled out ethanol at below 60° C. The reaction mixture was cooled down to room temperature. Water (2.5 L) was then added carefully at 20 to 35° C. The reaction mixture was then charged with Ethyl acetate (1.25 L). After complete addition of ethyl acetate, reaction mixture turned to clear solution. At room temperature it was stirred for 5 to 10 minutes and separated aqueous layer. Aqueous layer then again extracted with ethyl acetate (1.25 L) and separated aqueous layer. Combined organic layer then washed with twice 10% sodium bicarbonate solution (2×1.25 L) and twice process water (2×1.25 L) and separated aqueous layer. Organic layer then washed with 30% brine solution (2.5 L) and separated aqueous layer. Concentrated ethyl acetate in vacuo to get ethyl 2-iodobenzoate in 95% yield, as an oil, which was used in next the reaction, without any further purification. MS (ESI-MS): m/z 248.75 (M+H). $^1$H NMR (CDCl$_3$): 1.41-1.37 (t, 3H), 4.41-4.35 (q, 2H), 7.71-7.09 (m, 1H), 7.39-7.35 (m, 1H), 7.94-7.39 (m, 1H), 7.96-7.96 (d, 1H). HPLC Purity: 99.27%

Step-2 Process for the Preparation of ethyl 2-((tert-butoxycarbonyl)(cyclopropylmethoxy)amino)benzoate (XII-a)

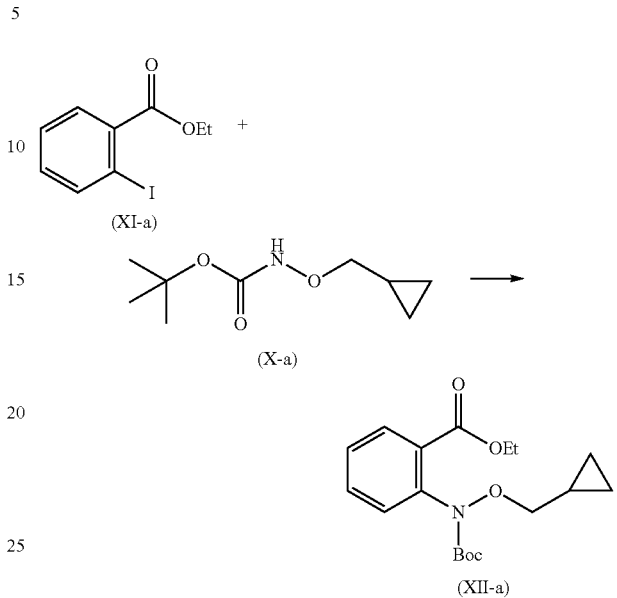

In a 5 L fixed glass assembly, toluene (1.5 L) was charged at room temperature. Copper (I) iodide (15.3 g, 0.08 mol) was added in one lot at room temperature. Glycine (39.1 g, 0.520 mol) was added in one lot at room temperature. Reaction mixture was stirred for 20 minutes at room temperature. Ethyl 2-iodobenzoate (221.2 g, 0.801 mol) was added in one lot at room temperature. Tert-butyl (cyclopropylmethoxy)carbamate (150 g, 0.801 mol) was added in one lot at room temperature. Reaction mixture was stirred for 20 minutes at room temperature. Potassium carbonate (885.8 g, 6.408 mol) and ethanol (0.9 L) were added at 25° C. to 35° C. Reaction mixture was stirred for 30 minutes. The reaction mixture was refluxed at 78 to 85° C. for 24 hours. Reaction mixture was cooled to room temperature and stirred for 30 minutes. The reaction mixture was then charged with ethyl acetate (1.5 L). After complete addition of ethyl acetate, reaction mixture turned to thick slurry. At room temperature it was stirred for 30 minutes and the solid inorganic material was filtered off through hyflow supercel bed. Inorganic solid impurity was washed with ethyl acetate (1.5 L), combined ethyl acetate layer was washed with twice water (2×1.5 L) and separated aqueous layer. Organic layer washed with 30% sodium chloride solution (1.5 L) and separated aqueous layer. Ethyl acetate was concentrated in vacuo to get ethyl 2-((tert-butoxycarbonyl)(cyclopropylmethoxy)amino)benzoate in 89% yield, as an oil, which was used in next the reaction, without any further purification. MS (ESI-MS): m/z 357.93 (M+Na). $^1$H NMR (CDCl$_3$): 0.26-0.23 (m, 2H), 0.52-0.48 (m, 2H), 1.10-1.08 (m, 1H), 1.38-1.35 (t, 3H), 1.51 (s, 9H), 3.78-3.76 (d, J=7.6 Hz, 2H), 4.35-4.30 (q, J=6.8 Hz, 2H), 7.29-7.25 (m, 1H), 7.49-7.47 (m, 2H), 7.78-7.77 (d, 1H). HPLC Purity: 88.07%

Step 3 Process for the Preparation of ethyl 2-((cyclopropylmethoxy)amino)benzoate (XIII-a)

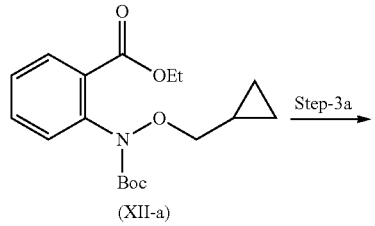
(XII-a)

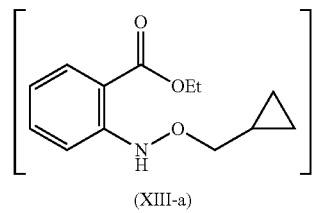
(XIII-a)

In a 10 L fixed glass assembly, dichloromethane (2.4 L) was charged at room temperature. Ethyl 2-((tert-butoxycarbonyl)(cyclopropylmethoxy)amino)benzoate (200 g, 0.596 mol) was charged and cooled externally with ice-salt at 0 to 10° C. Methanolic HCl (688.3 g, 3.458 mol, 18.34% w/w) solution was added slowly drop wise, over a period of 15 minutes, while maintaining internal temperature below 10° C. Reaction mixture was warmed to 20 to 30° C., and stirred at 20 to 30° C. for 3 hours. The reaction mixture was quenched with addition of water (3.442 L). Upon completion of water addition, the reaction mixture turn out to light yellow coloured solution. At room temperature it was stirred for another 15 minutes and separated aqueous layer. Aqueous layer was again extracted with Dichloromethane (0.8 L). Combined dichloromethane layer then washed with 20% sodium chloride solution (1.0 L) and separated aqueous layer. Concentrated dichloromethane vacuo to get Ethyl 2-((cyclopropylmethoxy)amino)benzoate in 92% yield, as an oil. MS (ESI-MS): m/z 235.65 (M+H)$^+$. $^1$H NMR (CDCl$_3$): 0.35-0.31 (m, 2H), 0.80-0.59 (m, 2H), 0.91-0.85 (m, 1H), 1.44-1.38 (t, 3H), 3.76-3.74 (d, 2H), 4.36-4.30 (q, 2H), 6.85-6.81 (t, 1H), 7.36-7.33 (d, 1H), 7.92-7.43 (m, 1H), 7.94-7.93 (d, 1H), 9.83 (s, 1H). HPLC Purity: 87.62%

Step 4 Process for the Preparation of ethyl 2N-(cyclopropylinethoxy)-3-ethoxy-3-oxopropanamido)benzoate (XIV-a)

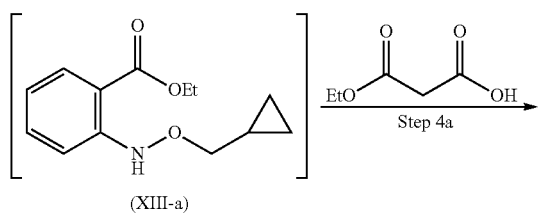
(XIII-a)

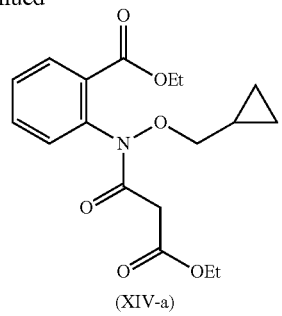
(XIV-a)

In a 2 L fixed glass assembly, Acetonitrile (0.6 L) was charged at room temperature. Ethyl 2-((cyclopropylmethoxy)amino)benzoate (120 g, 0.510 mol) was charged at room temperature. Ethyl hydrogen malonate (74.1 g, 0.561 mol) was charged at room temperature. Pyridine (161.4 g, 2.04 mol) was added carefully in to reaction mass at room temperature and cooled externally with ice-salt at 0 to 10° C. Phosphorous oxychloride (86.0 g, 0.561 mol) was added slowly drop wise, over a period of 2 hours, while maintaining internal temperature below 10° C. Reaction mixture was stirred at 0 to 10° C. for 45 minutes. The reaction mixture was quenched with addition of water (1.0 L). Upon completion of water addition, the reaction mixture turns out to dark red coloured solution. Dichloromethane (0.672 L) was charged at room temperature and it was stirred for another 15 minutes and separated aqueous layer. Aqueous layer was again extracted with dichloromethane (0.672 L). Combined dichloromethane layer then washed with water (0.400 L) and 6% sodium chloride solution (0.400 L) and separated aqueous layer. Mixture of acetonitrile and dichloromethane was concentrated in vacuo to get Ethyl 2-(N-(cyclopropylmethoxy)-3-ethoxy-3-oxopropanamido)benzoate in 95% yield, as an oil. MS (ESI-MS): m/z 350.14 (M+H)$^+$. $^1$H NMR (DMSO-d$_6$): 0.3-0.2 (m, 2H), 0.6-0.4 (m, 2H), 1.10-1.04 (m, 1H), 1.19-1.15 (t, 3H), 1.29-1.25 (t, 3H), 3.72-3.70 (d, 2H), 3.68 (s, 2H), 4.17-4.12 (q, 2H), 4.25-4.19 (q, 2H), 7.44-7.42 (d, 1H), 7.50-7.46 (t, 1H), 7.68-7.64 (m, 1H), 7.76-7.74 (d, 1H). HPLC Purity: 86.74%

Step 5: Process for the Preparation of ethyl 1-(cyclopropylmethoxy)-4-hydroxy-2-oxo-1,2 dihydroquinolline-3-carboxylate (XV-a)

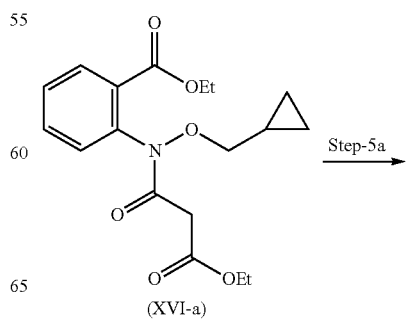
(XVI-a)

33
-continued

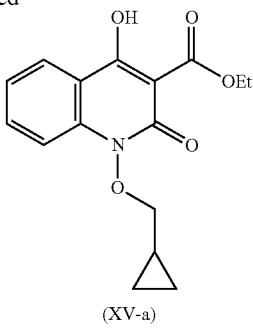

(XV-a)

In a 10 L fixed glass assembly under Nitrogen atmosphere, Methanol (0.736 L) was charged at room temperature. Ethyl 2-(N-(cyclopropylmethoxy)-3-ethoxy-3-oxopropanamido)benzoate (160 g, 0.457 mol) was charged at room temperature. Sodium methoxide powder (34.6 g, 0.641 mol) was added portion wise, over a period of 30 minutes, while maintaining internal temperature 10 to 20° C. Reaction mixture was stirred at 10 to 20° C. for 30 minutes. The reaction mixture was quenched with addition of ~1N aqueous hydrochloric acid solution (0.64 L) to bring pH 2, over a period of 20 minutes, while maintaining an internal temperature 10 to 30° C. Upon completion of aqueous hydrochloric acid solution addition, the reaction mixture turned to light yellow coloured slurry. Diluted the reaction mass with water (3.02 L) and it was stirred for another 1 hour. Solid material was filtered off and washed twice with water (2×0.24 L). Dried the compound in fan dryer at temperature 50 to 55° C. for 6 hours to get crude ethyl 1-(cyclopropylmetboxy)-4-hydroxy-2-oxo-1,2-dihydroquinoline-3-carboxylate as a solid.

Purification

In a 10 L fixed glass assembly, DMF (0.48 L) was charged at room temperature. Crude ethyl 1-(cyclopropylmethoxy)-4-hydroxy-2-oxo-1,2-dihydroquinoline-3-carboxylate (120 g) was charged at room temperature. Upon completion of addition of crude compound, clear reaction mass observed. Reaction mixture stirred for 30 minutes at room temperature. Precipitate the product by addition of water (4.8 L), over a period of 30 minutes, while maintaining an internal temperature 25 to 45° C. Upon completion of addition of water, the reaction mixture turned to light yellow colored slurry. Reaction mixture was stirred at 25 to 45° C. for 30 minutes. Solid material was filtered off and washed with water (0.169 L). Dried the product in fan dryer at temperature 50 to 55° C. for 6 hours to get pure ethyl 1-(cyclopropylmethoxy)-4-hydroxy-2-oxo-1,2-dihydroquinoline-3-carboxylate in 81% yield, as a solid. MS (ESI-MS): m/z 303.90 (M+H)$^+$. $^1$H NMR (DMSO-d$_6$): 0.37-0.35 (m, 2H), 0.59-0.55 (m, 2H), 1.25-1.20 (m, 1H), 1.32-1.29 (t, 3H), 3.97-3.95 (d, 2H), 4.36-4.31 (q, 2H), 7.35-7.31 (m, 1H), 7.62-7.60 (dd, 1H), 7.81-7.77 (m, 1H), 8.06-7.04 (dd, 1H). HPLC Purity: 95.52%

34
Step 6 Process for the Preparation of ethyl (1-(cyclopropylmethoxy)-4-hydroxy-2-oxo-1,2-dihydroquinoline-3-carbonyl)glycinate (XVI-a)

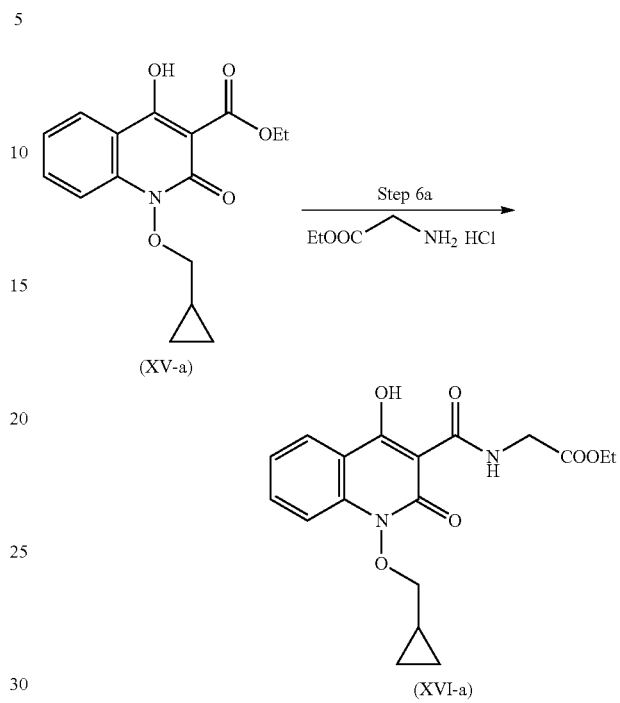

In a 5 L fixed glass assembly, tetrahydrofuran (0.5 L) was charged at room temperature. Ethyl 1-(cyclopropylmethoxy)-4-hydroxy-2-oxo-1,2-dihydroquinoline-3-carboxylate (100 g, 0.329 mol) was charged at room temperature. Glycine ethyl ester HCl (50.7 g, 0.362 mol) was charged at room temperature. N,N-Diisopropylethyl amine (64 g, 0.494 mol) was added carefully in to reaction mass at room temperature and heated the reaction mass at 65 to 70° C. Reaction mixture was stirred at 65 to 70° C. for 18 hours. The reaction mixture was quenched with addition of water (2.5 L).

Upon completion of water addition, the reaction mixture turns out to off white to yellow coloured slurry. Concentrated tetrahydrofuran below 55° C. in vacuo and reaction mixture was stirred at 25 to 35° C. for 1 hour. Solid material was filtered off and washed with water (3×0.20 L). Dried the compound in fan dryer at temperature 55 to 60° C. for 8 hours to get crude ethyl (1-(cyclopropylmethoxy)-4-hydroxy-2-oxo-1,2-dihydroquinoline-3-carbonyl)glycinate as a solid.

Purification

In a 2 L fixed glass assembly, Methanol (1.15 L) was charged at room temperature. Crude ethyl (1-(cyclopropylmethoxy)-4-hydroxy-2-oxo-1,2-dihydroquinoline-3-carbonyl)glycinate (100 g) was charged at room temperature. The reaction mass was heated to 65 to 70° C. Reaction mass was stirred for 1 h at 65 to 70° C. Removed heating and cool the reaction mass to 25 to 35° C. Reaction mass stirred for 1 h at 25 to 35° C. Solid material was filtered off and washed with methanol (0.105 L). The product was dried under fan dryer at temperature 55 to 60° C. for 8 hours to get pure ethyl 1-(cyclopropylmethoxy)-4-hydroxy-2-oxo-1,2-dihydroquinoline-3-carboxylate in 80% yield, as a solid. MS (ESI-MS):

m/z 360.85 (M+H)+. 1H NMR (DMSO-d6): 0.39 (m, 2H), 0.60-0.54 (m, 2H), 1.23-1.19 (t, 3H), 1.31-1.26 (m, 1H), 4.04-4.02 (d, 2H), 4.18-4.12 (q, 2H), 4.20-4.18 (d, 2H), 7.40-7.36 (m, 1H), 7.70-7.68 (d, 1H), 7.87-7.83 (m, 1H), 8.08-8.05 (dd, 1H), 10.27-10.24 (t, 1H). HPLC Purity: 99.84%

Step 7: Process for the Preparation of (1-(cyclopropylmethoxy)-4-hydroxy-2-oxo-1,2-dihydroquinoline-3-carbonyl)glycine (I-a)

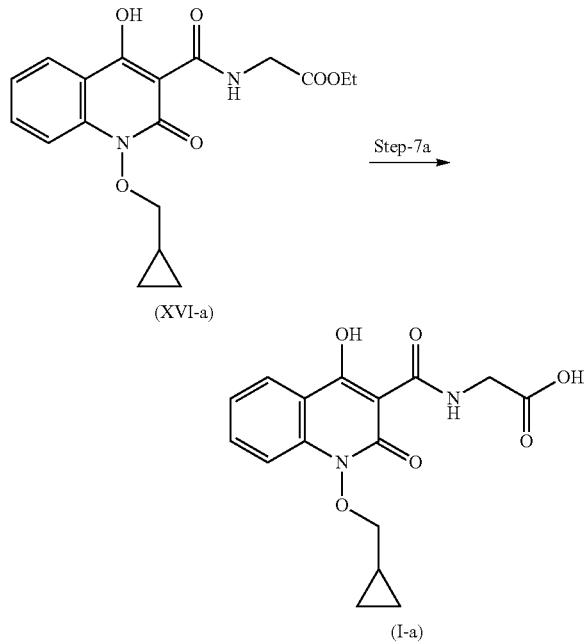

In a 5 L fixed glass assembly, methanol (0.525 L) was charged at room temperature. Ethyl 1-(cyclopropylmethoxy)-4-hydroxy-2-oxo-1,2-dihydroquinoline-3-carboxylate (75 g, 0.208 mol) was charged at room temperature. Water (0.30 L) was charged at room temperature. Sodium hydroxide solution (20.8 g, 0.520 mol) in water (0.225 L) was added carefully at 30 to 40° C. Upon completion of addition of sodium hydroxide solution, the reaction mass turned to clear solution. Reaction mixture stirred for 30 minutes at 30 to 40° C. Diluted the reaction by addition of water (2.1 L). Precipitate the solid by addition of hydrochloric acid solution (75 mL) in water (75 mL). Upon completion of addition of hydrochloric acid solution, the reaction mass turned to off white colored thick slurry. Reaction mixture was stirred for 1 h at room temperature. Solid material was filtered off and washed with water (4×0.375 L). The compound was dried under fan dryer at temperature 25 to 35° C. for 6 hours and then dried for 4 hours at 50 to 60° C. to get (1-(cyclopropylmethoxy)-4-hydroxy-2-oxo-1,2-dihydroquinoline-3-carbonyl) glycine in 98% yield, as a solid. MS (ESI-MS): m/z 333.05 (M+H)+. 1H NMR (DMSO-d6): 0.44-0.38 (m, 2H), 0.62-0.53 (m, 2H), 1.34-1.24 (m, 1H), 4.06-4.04 (d, 2H), 4.14-4.13 (d, 2H), 7.43-7.39 (t, 1H), 7.72-7.70 (d, 1H), 7.89-7.85 (m, 1H), 8.11-8.09 (dd, 1H), 10.27-10.24 (t, 1H), 12.97 (bs, 1H), 16.99 (s, 1H). HPLC Purity: 99.85%

Polymorphic Data (XRPD):

| 2θ | d value | Relative Intensity |
|---|---|---|
| 8.0° ± 0.2° | 11.07 | 77.0% |
| 8.9° ± 0.2° | 9.96 | 100.0% |
| 10.6 ± 0.2° | 8.27 | 30.5% |
| 11.3 ± 0.2° | 7.78 | 38.1% |
| 16.1 ± 0.2° | 5.50 | 24.1% |
| 25.5 ± 0.2° | 3.48 | 63.0% |
| 26.4 ± 0.2° | 3.36 | 32.3% |

Example 2.

Example 2a. Process for Preparation of 2-(cyclopropylmethoxy)isoindoline-1,3-dione: (Compound VIII)

In a 100 mL rbf, charged N-hydroxyphthalimide (10 g, 0.0613 mol), Cyclopropyl methyl bromide (9.93 g, 0.0735 mol) in DMF (30 mL). Cooled to 0 to 5° C. Added dropwise DBU (12.13 g, 0.0796 mol) at 0 to 10° C. Warmed Reaction mixture to 35 to 40° C. and stirred for 2 hrs. at 35 to 40° C. Added reaction mass dropwise into previously cooled 0.5 N HCl solution (300 mL) at 0 to 10° C. to get solid precipiation. Stirred reaction mass for 1 hr. at 0 to 10° C. Filtered the product. Washed with water (2×50 mL). Dried in hot air oven at 50 to 55° C. for 6 hrs. Dry weight (11.2 g) product obtained in 84% yield, HPLC Purity: 99.48%

Example 2b. Process for Preparation of 2-(cyclopropylmethoxy)isoindoline-1,3-dione: (Compound VIII)

In a 500 mL 3-nrbf, MTBE (30 mL) was charged at room temperature. N-hydroxyphthalimide (20 g, 0.122 mol) was added in one lot at room temperature. Cyclopropyl methyl bromide (21.52 g, 0.159 mol) was added carefully at room temperature. Cooled the reaction mixture to 0 to 10° C. Triethyl amine (19.85 g, 0.196 mol) solution in MTBE (30 mL) was added carefully at 0 to 10° C. Upon completion of Triethyl amine addition, reaction mixture turns out to be clear solution. Reaction mixture was stirred for 72 hrs at 25 to 35° C. The reaction mixture was then charged with Ethyl acetate (100 mL) at room temperature and it was stirred for 30 minutes and the organic layer was separated. Aqueous layer was again extracted with ethyl acetate (1×100 mL). Combined ethyl acetate layer then washed with 1N HCl solution (1×100 mL) and 5% NaHCO3 solution (1×50 mL) and separated aqueous layer. Organic layer then washed with water (2×50 mL) and 20% brine solution (1×100 mL) and separated aqueous layer. Concentrated ethyl acetate in vacuo to get solid product in 59% yield.

Example 2c. Process for Preparation of 2-(cyclopropylmethoxy)isoindoline-1,3-dione: (Compound VIII)

In a 100 mL 3-nrbf, charged N-hydroxyphthalimide (2 g, 0.0123 mol), Cyclopropyl methyl bromide (1.99 g, 0.0147 mol) in DMF (6 mL). Cooled to 0 to 5° C. Added dropwise N,N-Diisopropylethyl amine (3.17 g, 0.0245 mol) at 0 to 10° C. Reaction mixture was heated to 50 to 60° C. and stirred for 20 hrs. at 50 to 60° C. Cooled reaction mass to 25 to 35° C. Added dropwise 0.5 N HCl solution (50 mL) at 0 to 10° C. to get solid precipiation. Adjust pH of reaction mass to 7.5 to 8 using 10% sodium bicarbonate solution below 35° C. Stirred reaction mass for 1 hr. at 25 to 35° C. Filtered the product. Washed with water (2×10 mL). Dried in hot air oven at 50 to 55° C. for 2 hrs. Dry weight (2.2 g) product obtained in 83%. yield, HPLC Purity: 99.59%

Example 3

Example 3a. Process for the Preparation of ethyl 2-((tert-butoxycarbonyl)(cyclopropylmethoxy) amino)benzoate (XII-a)

In a 250 mL 3-nrbf, toluene (240 mL) was charged at room temperature. Copper (I) iodide (2.441 g, 12.82 mmol) was added in one lot at room temperature. Glycine (6.25 g, 83 mmol) was added in one lot at room temperature. Ethyl 2-iodobenzoate (46 g, 167 mmol) was added in one lot at room temperature. Tert-butyl (cyclopropylmethoxy)carbamate (24 g, 128 m mol) was added in one lot at room temperature. Reaction mixture was stirred for 20 minutes at room temperature. Caesium carbonate (62.6 g, 192 mmol) were added at 25° C. to 35° C. Reaction mixture was stirred for 30 minutes. The reaction mixture was refluxed at 100 to 105° C. for 24 hours. Reaction mixture was cooled to room temperature and stirred for 30 minutes. The reaction mixture was then charged with ethyl acetate (100 mL). After complete addition of ethyl acetate, reaction mixture turned to thick slurry. At room temperature it was stirred for 30 minutes and the solid inorganic material was filtered off through hyflow supercel bed. Inorganic solid impurity was washed with ethyl acetate. Combined Ethyl acetate was concentrated in vacuo to get crude (57.2 g) ethyl 2-((tert-butoxycarbonyl)(cyclopropylmethoxy)amino)benzoate.
Pure (38.2 g) of ethyl 2-((tert-butoxycarbonyl)(cyclopropylmethoxy)amino)benzoate obtained after column chromatography in 89% yield, as an oil. HPLC Purity: 93%

Example 3b. Process for the Preparation of ethyl 2-((tert-butoxycarbonyl)(cyclopropylmethoxy) amino)benzoate (XII-a)

In a 50 mL rbf, Charged copper(I) iodide (0.203 g, 1.068 mmol)) and 1,10-Phenanthroline (0.962 g, 5.34 mmol) in toluene (14 ml). Stirred and charged ethyl 2-iodobenzoate (3.83 g, 13.89 mmol)), tert-butyl cyclopropylmethoxycarbamate (2.0 g, 10.68 mmol) respectively. Reaction mixture was stirred for 20 minutes at room temperature. Charged cesium carbonate (5.22 g, 16.02 mmol)). Heated to 80° C. Stirred the reaction mass for 24 h at 80-85° C. Reaction mass cooled to room temperature. Charged ethyl acetate (20 mL) and stirred for 30 minutes. Filtered. Filterated evaporated to get (4.46 g). Pure (2.43 g) of ethyl 2-((tert-butoxycarbonyl) (cyclopropylmethoxy)amino)benzoate obtained after column chromatogrphy using ethyl acetate in hexane. 68% yield, as an oil. HPLC Purity: 98.37%

Example 4 Process for the Preparation of ethyl 2-((cyclopropylmethoxy)amino)benzoate (XIII-a)

In a 50 mL 3-nrbf, Charged Ethyl 2-((tert-butoxycarbonyl)(cyclopropylmethoxy)amino)benzoate (0.5 g, 0.00149 mol) and p-Toluene sulphonic acid in Methanol (3 mL). Reaction mixture was heated to 35 to 40° C. and stirred at 35 to 40° C. for 4 hours. The reaction mixture was quenched with addition of water (10 mL). Extracted with Dichloromethane (10 mL×2). Combined dichloromethane layer then washed with water (10 mL). Dichloromethane layer dried over sodium sulphate. Dichloromethane layer concentrated in vacuo to get Ethyl 2-((cyclopropylmethoxy)amino) benzoate (0.35 g) as an oil. HPLC Purity 90.8%.

Example 5. Process for the Preparation of ethyl 1-(cyclopropylmethoxy)-4-hydroxy-2-oxo-1,2 dihydroquinoline-3-carboxylate (XV-a)

In a 250 mL 3-nrbf under Nitrogen atmosphere, Ethanol (45 mL) was charged at room temperature. Ethyl 2-(N-(cyclopropylmethoxy)-3-ethoxy-3-oxopropanamido)benzoate (10 g, 0.028 mol) was charged at room temperature. Sodium ethoxide powder (2.92 g, 0.042 mol) was added portion wise, over a period of 30 minutes, while maintaining internal temperature 10 to 20° C. Reaction mixture was stirred at 10 to 20° C. for 30 minutes. The reaction mixture was quenched with addition of ~1N aqueous hydrochloric acid solution (40 mL) to bring pH 2, over a period of 20 minutes, while maintaining an internal temperature 10 to 30° C. Upon completion of aqueous hydrochloric acid solution addition, the reaction mixture turns out to light yellow coloured slurry. Diluted the reaction mass with water (187.5 mL) and it was stirred for another 1 hour. Solid material was filtered off and washed twice with water (2×15 mL). Dried the compound in fan dryer at temperature 50 to 55° C. for 6 hours to get cnide ethyl 1-(cyclopropylmethoxy)-4-hydroxy-2-oxo-1,2-dihydroquinoline-3-carboxylate as a solid in 92% yield.

Example 6. Process for the Preparation of ethyl (1-(cyclopropylmethoxy)-4-hydroxy-2-oxo-1,2-dihydroquinoline-3-carbonyl)glycinate (XV-a)

In a 2 L 3-nrbf, 1, 4-Dioxane (275 mL) was charged. Charged Cyclized product (65 g),Glycine ethyl ester hydrochloride (32.96 g), Diisopropylethylamine (DIPEA) (33.22 g) and flush with 1,4-Dioxane (50 mL). Stirred the reaction mass for 5 minutes. The reaction mixture was heated at 90 to 100° C. in an oil bath and stirred for 18 h at 90 to 100° C. Reaction monitored by HPLC. Cooled reaction mass to 50 to 60° C. Distilled out 1, 4-Dioxane under vacuum below 60° C. Cooled reaction mass to 25 to 35° C. Add Process water (390 mL). Stirred it for 1 h at 25-35° C. Filtered the product. Washed the solid with Process water (130 mL×3). Suck dried for 1 h. Dry the product crude Glycine coupled product in a hot air oven for 8 h at 55 to 60° C.

Purification

The crude Glycine coupled product was refluxed in Methanol (720) at 60 to 70° C. for 1 h. The reaction mixture was then cooled to 25 to 35° C. and stirred for 1 h. The solid was filtered using a Buchner funnel and washed with methanol (72 mL). Suck dried for 1 h. Dry it in a hot air oven at 55 to 60° C. for 6 h to afford pure Glycine coupled product, Yield 83%.

Example 7 Process for the Preparation of Intermediate ethyl 2-((tert-butoxycarbonyl)(cyclopropylmethoxy)amino)benzoate (XII-a)

Step 1 Preparation of tert-butyl (cyclopropylmethoxy)carbamate (X-a)

Process for the preparation of tert-butyl (cyclopropylmethoxy)carbamate is further divided in four steps (i.e. Step A', B', C' and D')

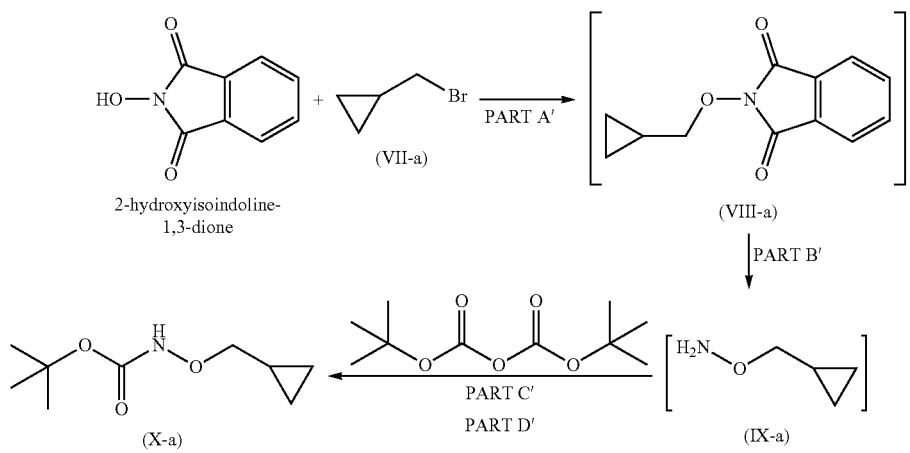

Part-A': Process for Preparation of 2-(cyclopropylmethoxy)isoindoline-1,3-dione (VIII-a):

In a 5 L fixed glass assembly, DMSO (1.0 L) was charged at room temperature. N-hydroxyphthalimide (200 g, 1.226 mol) was added in one lot at room temperature. Potassium carbonate (271 g, 1.961 mol) was added carefully at room temperature. After complete addition of potassium carbonate, reaction mixture turned out to thick slurry. Cyclopropyl methyl bromide (198.7 g, 1.471 mol) was added carefully at room temperature. Reaction mixture was stirred for 3 hrs at 45 to 55° C. Reaction mixtures cooled to room temperature and dump the reaction mass in to cold water (5.0 L). The reaction mixture was then charged with ethyl acetate (2.0 L). After complete addition of ethyl acetate, reaction mixture turns out to be clear solution. At room temperature it was stirred for 30 minutes and the organic layer was separated. Aqueous layer was again extracted twice with ethyl acetate (1×2.0 L) and (1×1.0 L). Combined ethyl acetate layer then wash twice with water (2×1.0 L) and 20% brine solution (1.0 L) and separated aqueous layer. Ethyl acetate was concentrated in vacuo to get solid product, which used in the next (Part-B) reaction, without any further purification.

Part-B': Process for Preparation of O-(cyclopropylmethyl)hydroxylamine (IX-a)

DCM (2.0 L) was added in to solid product obtained in part-A at room temperature. The reaction mixture was cooled down to 0 to 10° C. Hydrazine hydrate (117.9 g, 2.353 mol) was added carefully at 0 to 10° C. After complete addition of hydrazine hydrate the reaction mixture turned to thick slurry. Reaction mixture was stirred for 18 hrs at 20 to 35° C. Solid organic material was filtered off through supercel bed. Organic solid impurity was removed by washing with DCM twice, combined all filtrate again wash with twice water and separated aqueous layer. Organic layer washed with 20% sodium chloride solution (0.8 L) and separated aqueous layer. Organic layer was used in next (Part-C) reaction without any further purification.

Part-C' and Part D': Process for the preparation of tert-butyl (cyclopropylmethoxy)carbamate (X-a)

Part-C'

Organic layer obtained from part-B cool to 0 to 5° C. Sodium carbonate (249.5 g, 2.353 mol) added at 0 to 5° C. Boc anhydride (205.5 g, 0.944 mol) was added carefully at 0 to 5° C. Upon completion of addition of Boc anhydride the reaction mass turn to be thick slurry. Stir reaction mixture for 1 hour at 0 to 5° C. Cooling was removed and reaction mixture was stirred for 18 hrs at 20 to 35° C. Inorganic solid further filtered off and wash with twice DCM (2×0.2 L). Combined filtrate, which was used in next (Part-D) reaction, without any further purification.

Part-D'

Organic layer obtained from part-C and imidazole (64.1 g, 0.944 mol) were mixed carefully at 20 to 35° C. Reaction mixture was stirred for 20 hours at 20 to 35° C. Reaction mixture then washed with thrice aqueous hydrochloric acid solution in water and separated aqueous layer. Organic layer was then washed with water and 20% brine solution and separated aqueous layer. DCM was concentrated in vacuo to get tert-butyl (cyclopropylmethoxy)carbamate in 68% yield, as an oil, which was used in next the reaction, without any further purification.

Step 1'a Process for Preparation of ethyl 2-iodobenzoate (XI-a)

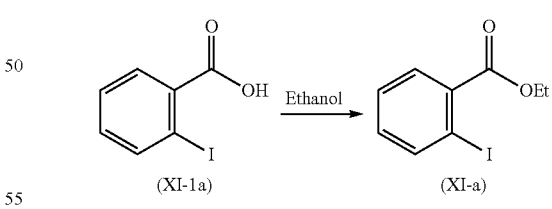

In a 5 L fixed glass assembly, Ethanol (1.25 L) charged at room temperature. 2-iodobenzoic acid (250 g, 1.00 mol) was added in one lot at room temperature. Sulphuric acid (197.7 g, 2.01 mol) was added carefully in to reaction mixture at 20 to 35° C. The reaction mixture was heated to 80 to 85° C. Reaction mixture was stirred for 20 hours at 80 to 85° C. After completion of reaction distilled out ethanol at below 60° C. The reaction mixture was cooled down to room temperature. Water (2.5 L) was then added carefully at 20 to 35° C. The reaction mixture was then charged with Ethyl acetate (1.25 L). After complete addition of ethyl acetate, reaction mixture turned to clear solution. At room temperature it was stirred for 5 to 10 minutes and separated aqueous layer. Aqueous layer then again extracted with ethyl acetate (1.25 L) and separated aqueous layer. Combined organic layer then washed with twice 10% sodium bicarbonate solution (2×1.25 L) and twice process water (2×1.25L) and separated aqueous layer. Organic layer then washed with 30% brine solution (2.5 L) and separated aqueous layer. Concentrated ethyl acetate in vacuo to get ethyl 2-iodobenzoate in 95% yield, as an oil, which was used in next the reaction, without any further purification. MS (ESI-MS): m/z 248.75 (M+H). $^1$H NMR (CDCl$_3$): 1.41-1.37 (t, 3H), 4.41-4.35 (q, 2H), 7.71-7.09 (m, 1H), 7.39-7.35 (m, 1H), 7.94-7.39 (m, 1H), 7.96-7.96 (d, 1H).

Step-2 Process for the Preparation of ethyl 2-((tert-butoxycarbonyl)(cyclopropylmethoxy)amino)benzoate (XII-a)

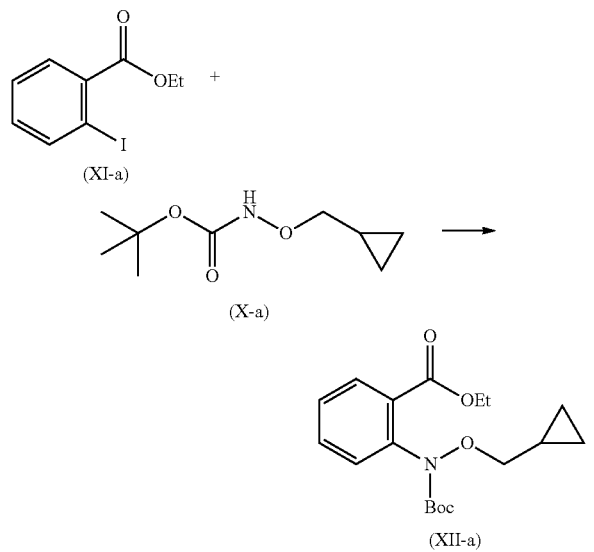

In a 5 L fixed glass assembly, toluene (1.5 L) was charged at room temperature. Copper (I) iodide (15.3 g, 0.08 mol) was added in one lot at room temperature. Glycine (39.1 g, 0.520 mol) was added in one lot at room temperature. Reaction mixture was stirred for 20 minutes at room temperature. Ethyl 2-iodobenzoate (221.2 g, 0.801 mol) was added in one lot at room temperature. Tert-butyl (cyclopropylmethoxy)carbamate (150 g, 0.801 mol) was added in one lot at room temperature. Reaction mixture was stirred for 20 minutes at room temperature. Potassium carbonate (885.8 g, 6.408 mol) and ethanol (0.9 L) were added at 25° C. to 35° C. Reaction mixture was stirred for 30 minutes. The reaction mixture was refluxed at 78 to 85° C. for 24 hours. Reaction mixture was cooled to room temperature and stirred for 30 minutes. The reaction mixture was then charged with ethyl acetate (1.5 L). After complete addition of ethyl acetate, reaction mixture turned to thick slurry. At room temperature it was stirred for 30 minutes and the solid inorganic material was filtered off through hyflow supercel bed. Inorganic solid impurity was washed with ethyl acetate (1.5 L), combined ethyl acetate layer was washed with twice water (2×1.5 L) and separated aqueous layer. Organic layer washed with 30% sodium chloride solution (1.5 L) and separated aqueous layer. Ethyl acetate was concentrated in vacuo to get ethyl 2-((tert-butoxycarbonyl)(cyclopropylmethoxy)amino)benzoate in 89% yield, as an oil, which was used in next the reaction, without any further purification. MS (ESI-MS): m/z 357.93 (M+Na). $^1$H NMR (CDCl$_3$): 0.26-0.23 (m, 2H), 0.52-0.48 (m, 2H), 1.10-1.08 (m, 1H), 1.38-1.35 (t, 3H), 1.51 (s, 9H), 3.78-3.76 (d, J=7.6 Hz, 2H), 4.35-4.30 (q, J=6.8 Hz, 2H), 7.29-7.25 (m, 1H), 7.49-7.47 (m, 2H), 7.78-7.77 (d, 1H).

Example 8 Process for the Preparation of (1-(cyclopropylmethoxy)-4-hydroxy-2-oxo-1,2-dihydroquinoline-3-carbonyl)glycylglycine (XVII)

Step 1 Process for the Preparation of ethyl (1-(cyclopropylmethoxy)-4-hydroxy-2-oxo-1,2-dihydroquinoline-3-carbonyl)glycylglycinate (XVII-1)

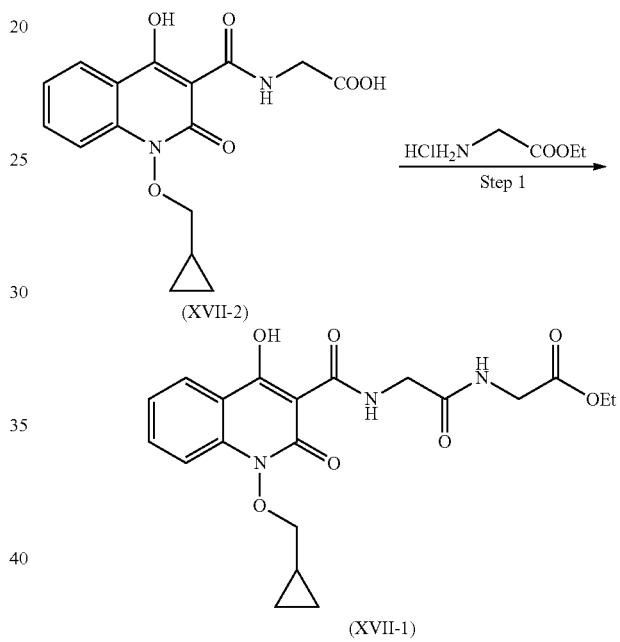

Process

A solution of Ethyl glycinate hydrochloride (10.08 g, 0.072 mol) in N, N-Dimethyl acetamide (40 mL) was treated under stirring with Triethyl amine (21.1 mL, 0.15 mol) at 5° C. to 10° C. Reaction mass then treated with (1-(cyclopropylmethoxy)-4-hydroxy-2-oxo-1,2-dihydroquinoline-3-carbonyl)glycine (XVII-2) (20.0 g, 0.060 mol), Benzotriazol-1-ol (80.12 g, 0.592 mol) in THF (100 mL) and N-N-Dimethyl acetamide (20 mL) at 5 to 10° C. Reaction mass was stirred at 5 to 10° C. for 15 minutes. Cool the reaction mass to −5° C. to −10° C. Added solution of N,N'-dicyclohexylcarbodiimide (14.88 g, 0.072 mol) in N, N-Dimethyl acetamide (40 mL). Reaction mixture was stirred at −5° C. to −10° C. for 1.5 h. Remove cooling and warm reaction mixture to room temperature. Reaction mixture was stirred for 16 h at room temperature. Filter the solid. Evaporated filtrate under vacuum at below 60° C. Solid material obtained was dissolved in Chloroform (200 mL) and stirred it for 30 minutes at room temperature and filtered and collected filtrate. Washed filtrate with sodium bicarbonate and brine solution. Evaporated solvents from organic layer under reduced pressure to get white colored solid which is purified using Hexane to get ethyl (1-(cyclopropylmethoxy)-4-hydroxy-2-oxo-1,2-dihydroquinoline-3-carbonyl)glycylglycinate (XVII-1) as a white colored solid with 86% yield.

Step 2: Preparation of (1-(cyclopropylmethoxy)-4-hydroxy-2-oxo-1,2-dihydroquinoline-3-carbonyl)glycylglycine (XVII)

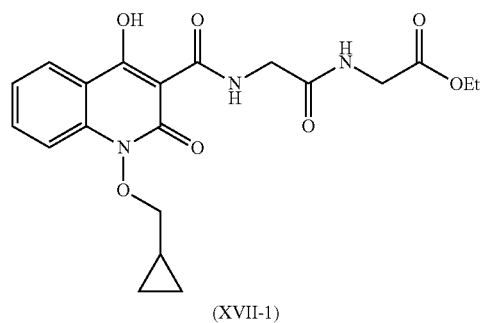

Process

A solution of Ethyl (1-(cyclopropylmethoxy)-4-hydroxy-2-oxo-1,2-dihydroquinoline-3-carbonyl)glycylglycinate (II) (21.3 g, 0.051 mol) in methanol (149 ml) and water (85.2 ml) was treated under stirring with solution of sodium hydroxide (5.10 g, 0.127 mol) in water (63.9 mL) at room temperature. Reaction mixture was stirred for 30 min. at room temperature. Reaction mixture was acidified using dilute HCl up to pH-2. Precipitated solid was filtered to get (1-(cyclopropylmethoxy)-4-hydroxy-2-oxo-1,2-dihydroquinoline-3-carbonyl)glycylglycine with 71% yield. $^1$H NMR (DMSO-d6): 0.38-0.37 (d, 2H), 0.59-0.57 (d, 2H), 1.18-1.15 (m, 1H), 3.82-3.81 (d, 2H), 4.04-4.02 (d, 2H), 4.11-4.09 (d, 2H), 7.41-7.37 (m, 1H), 7.71-7.69 (d, 1H), 7.87-7.83 (m, 1H), 8.09-8.07 (d, 1H), 8.48 (s, 1H), 10.41 (s, 1H), 12.69 (bs, 1H), 17.07 (s, 1H).

Example 9 Process for the Preparation of (1-(cyclopropylmethyl)-4-hydroxy-2-oxo-1,2-dihydroquinoline-3-carbonyl)glycine (XVIII)

Step 1 Preparation of ethyl 2-nitrobenzoate (XVIII-6)

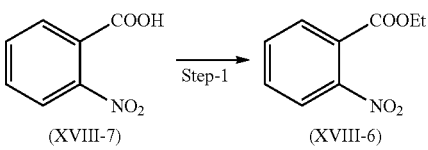

To a stirring solution of 2-Nitrobenzoic acid (II) (2.0 Kg, 11.96 mol) in Acetone (10 L) was added sodium bicarbonate (1.21 Kg, 14.40 mol) and diethyl sulfate (1.93 Kg, 12.51 mol). Reaction mixture was stirred at 55 to 60° C. for 10 h. Distilled out solvent from reaction mass to get thick slurry. Reaction mass was then diluted with water. Extracted with ethyl acetate. Ethyl acetate layer then washed with brine solution. Ethyl acetate layer was concentrated under reduced pressure to get ethyl 2-nitrobenzoate (XVIII-6) as a pale yellow colored liquid with 99% yield.

Step 2: Preparation of ethyl 2-aminobenzoate (XVIII-5)

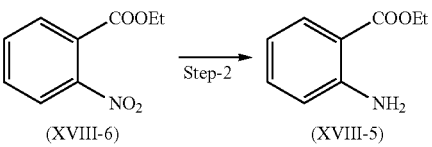

To a stirring solution of ethyl 2-nitrobenzoate (XVIII-6) (300 g, 1.53 mol) in mixture of methanol (2100 ml) and Tetrahydrofuran (2100 ml) was added portion wise stannous chloride dihydrate (4.61 mol) at room temperature. Reaction mixture was stirred at 25 to 35° C. for 18 h. Reaction mixture was diluted with water and basified with aqueous sodium bicarbonate solution. Product was extracted with ethyl acetate. Ethyl acetate layer concentrated under reduced pressure to get ethyl 2-aminobenzoate (XVIII-5) as a pale yellow colored liquid with 87% yield.

Step-3. Preparation of ethyl 2-((cyclopropylmethyl)amino)benzoate (XVIII-4)

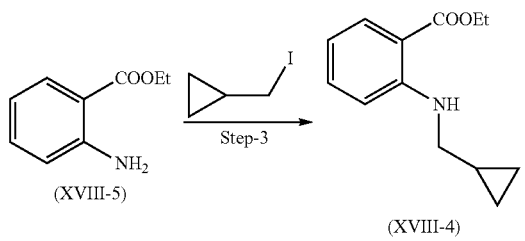

To a stirring solution of Iodomethyl cyclopropane (45.26 g, 24.8 mmol) in DMF (63.2 mL) was added Caesium carbonate (80.8 g, 24.8 mmol). Cool to 10° C. to 15° C. To this was added solution of ethyl 2-aminobenzoate (31.6 g, 19.1 mmol) in DMF (63.2 mL). Stirred reaction mixture for 18 h at ambient temperature. Reaction mixture was diluted with water. Extract reaction mixture with Ethyl acetate. Ethyl acetate layer was washed with brine solution. Solvent evaporated under reduced pressure to get crude product which was column purified using 0-1% Ethyl acetate in hexane to get ethyl 2-((cyclopropylmethypamino)benzoate (XVIII-4) as a pale yellow colored liquid with 22% yield.

Step-4. Preparation of ethyl 2-(N-(cyclopropylmethyl)-3-ethoxy-3 oxopropanamido)benzoate (XVIII-3)

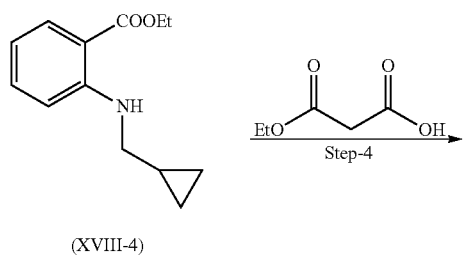

(XVIII-4)

To a stirring solution of 3-ethoxy-3-oxopropanoic acid (18.75 g, 1.42 mmol) and ethyl 2-((cyclopropylmethyl)amino)benzoate (28.3 g, 1.29 mmol) in acetonitrile (141.5 ml) was added pyridine (41.8 mL, 5.16 mmol) and reaction mixture was cooled to 0 to 5° C. To this was added POCl₃ (14.4 mL, 1.55 mmol) at 0 to 5° C. over 1.5 h. Stirred reaction mass for 30 min. Reaction mixture was diluted with water. Product extracted with Dichloromethane. Dichloromethane layer washed with water and brine solution. Evaporated solvent under reduced pressure to get ethyl 2-(N-(cyclopropyhnethyl)-3-ethoxy-3 oxopropanamido)benzoate (XVIII-3) as a red colored liquid with 100% yield.

Step-5. Preparation of ethyl 1-(cyclopropylmethyl)-4-hydroxy-2-oxo-1,2-dihydroquinoline-3-carboxylate (XVIII-2)

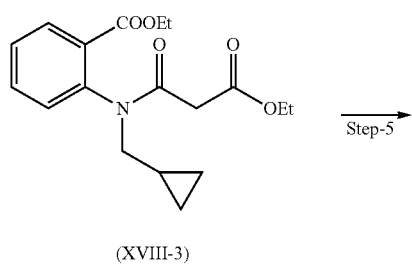

(XVIII-3)

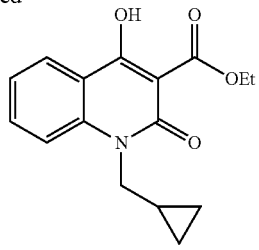

(XVIII-2)

To a stirring solution of ethyl 2-(N-(cyclopropylmethyl)-3-ethoxy-3 oxopropanamido)benzoate (XVIII-3) (43.0 g, 1.29 mmol) in Methanol (193.5 mL) was added portion wise sodium methoxide (17.42 g, 3.22 mmol) at 10 to 15° C. Reaction mixture was stirred for 1 h. at 15 to 20° C. Excess methanol was distilled out and then reaction mixture diluted with Hydrochloric acid solution to bring pH ~2. Precipitated product was filtered and dried to get ethyl 1-(cyclopropylmethyl)-4-hydroxy-2-oxo-1,2-dihydroquinoline-3-carboxylate (XVIII-2) with 91% yield.

Step-6. Preparation of ethyl (1-(cyclopropylmethyl)-4-hydroxy-2-oxo-1,2-dihydroquinoline-3-carbonyl)glycinate (XVIII-1)

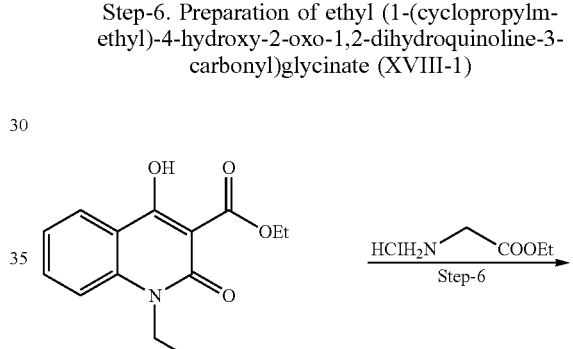

(XVIII-1)

To a stirring solution of ethyl 1-(cyclopropylmethyl)-4-hydroxy-2-oxo-1,2-dihydroquinoline-3-carboxylate (XVIII-2) (33.6 g, 1.16 mmol) in 1, 4-Dioxne (168 ml) was added glycine ethylester HCl (17.95 g, 1.29 mmol) and Di isopropylethyl amine (24.18 mL, 1.4 mmol) at room temperature. Reaction mixture was stirred for 18 h. at 90 to 100° C. Excess 1, 4-Dioxane was distilled out and then reaction mixture diluted with water. Precipitated product was filtered and dried to get crude compound. Crude compound was purified by refluxing it with methanol for 1 hr., cooled to room temperature and filtered the product to get ethyl (1-(cyclopropylmethyl)-4-hydroxy-2-oxo-1,2-dihydroquinoline-3-carbonyl)glycinate (XVIII-1) with 77% yield.

Step-7. Preparation of (1-(cyclopropylmethyl)-4-hydroxy-2-oxo-1,2-dihydroquinoline-3-carbonyl) glycine (XVIII)

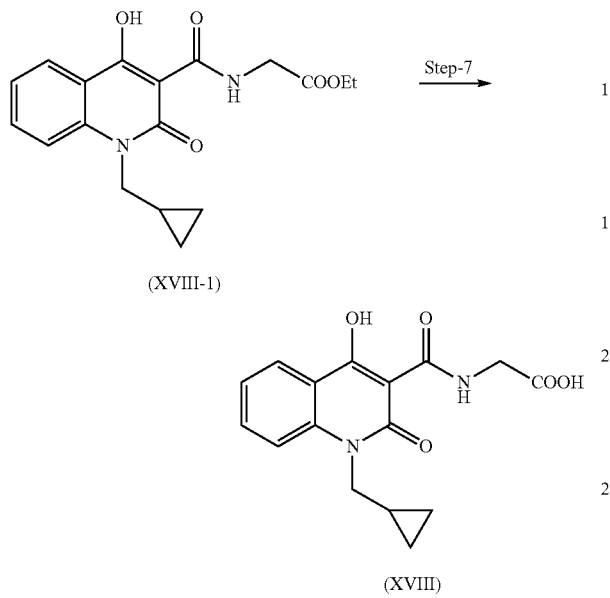

(XVIII-1)

(XVIII)

To a stirring solution of ethyl (1-(cyclopropylmethyl)-4-hydroxy-2-oxo-1,2-dihydroquinoline-3-carbonyl)glycinate (XVIII-1) (30.5 g, 8.85 mmol) in mixture of methanol (215.95 ml) and water (122 ml) was added slowly solution of sodium hydroxide (8.85 g, 2.21 mmol) in water (91.5 mL) at room temperature. Reaction mixture was stirred for 30 min. at room temperature. Reaction mixture was acidified using dilute HCl up to pH-2. Precipitated solid was filtered to get (1-(cyclopropylmethyl)-4-hydroxy-2-oxo-1,2-dihydroquinoline-3-carbonyl)glycine (XVIII) with 96% yield.

$^1$H NMR (DMSO-d6): 0.42-0.46 (d, 4H), 1.28-1.18 (m, 1H), 4.11-4.12 (d, 2H), 4.21-4.19 (d, 2H), 7.33-7.36 (t, 1H), 7.71-7.69 (t, 1H), 7.81-7.80 (d, 1H), 8.06-8.08 (t, 1H), 10.52-10.54 (t, 1H), 12.94 (s, 1H).

Example 10 Process for the Preparation of (1-butoxy-4-hydroxy-2-oxo-1,2-dihydroquinoline-3-carbonyl)glycine (XIX)

Step-1. Preparation of 2-butoxyisoindoline-1,3-Dione (XIX-8)

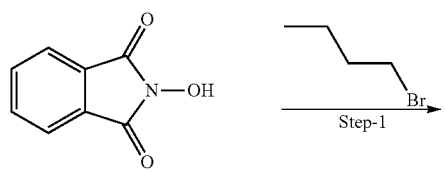

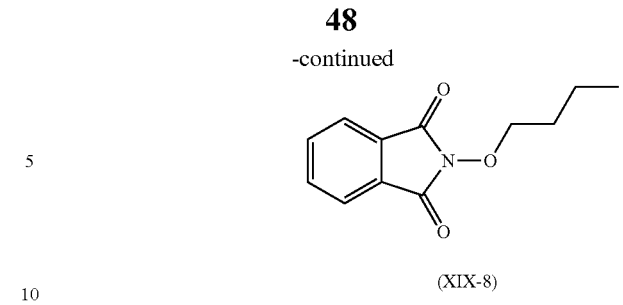

(XIX-8)

To a stirring solution of 2-hydroxyisoindoline-1,3-dione (25 g, 0.153 mol), Potassium carbonate (33.9 g, 0.245 mol) in DMSO (25 ml) was added slowly 1-Bromobutane (25.2 g, 0.184 mol) at room temperature. Reaction mixture was stirred at 45 to 55° C. for 3 h. Dump the reaction mixture in to cold water followed by extraction with Ethyl acetate and separated the organic layer. Washed organic layer with water and evaporated solvent under reduced pressure to get 2-butoxyisoindoline-1, 3-Dione (XIX-8) as a Pale yellow colored liquid with 90% yield.

Step-2. Preparation of tert-butyl butoxycarbamate (XIX-6)

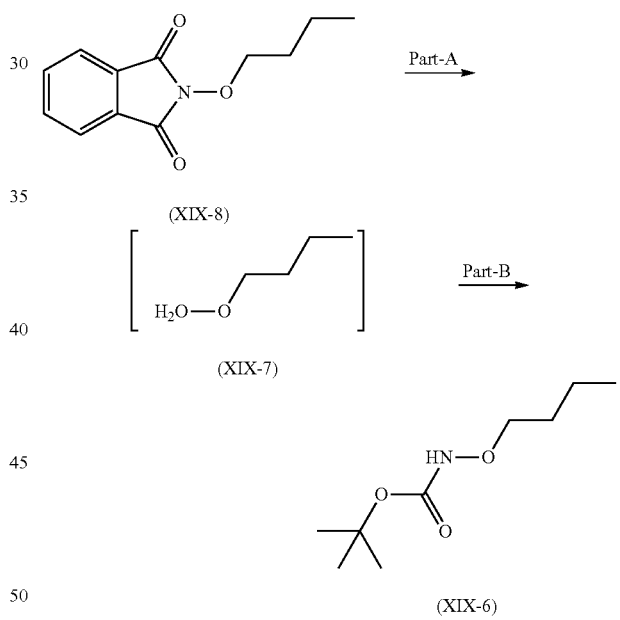

A solution of 2-butoxyisoindoline-1, 3-dione (XIX-8) (29 g, 0.132 mol) in dichloromethane (232 ml) was treated under stirring with Hydrazine hydrate (13.24 g, 0.265 mol) at 0 to 5 oC. The cooling bath was removed and the reaction mixture was stirred at room temperature for 18 h. Filter the reaction mixture followed by wash with dichloromethane then washed filtrate with water and then brine solution and separated organic layer contain O-butylhydroxylamine (XIX-7). Charged organic layer into another flask and cooled to 0 to 5° C. Sodium carbonate (28.02 g, 0.265 mole) was added portion wise. Di-tert-butyl-dicarbonate (23.10 g, 0.106 mol) was added into the reaction mixture. Stirred reaction mixture for 1 hour. The cooling bath was removed and the reaction mixture was stirred for 20 hours at room temperature. The reaction mixture was filtered off then washed with DCM containing crude tert-butyl butoxycarbamate. Charged organic layer into another clean and dry flask. Imidazole (7.20 g, 0.106 mole) was added at room temperature. Stirred reaction mixture for 20 hours at room temperature. The reaction mixture was washed with dil. HCl solution then water and brine and separated the organic layer. Dried organic layer over sodium sulphate and evaporated under reduced pressure to get tert-butyl butoxycarbamate (XIX-6) as a pale yellow colored liquid with 70% yield.

Step-3. Preparation of ethyl 2-iodobenzoate (XI-a)

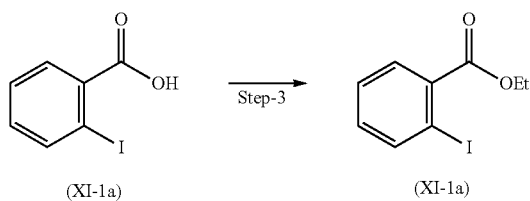 [SMILES: O=C(O)c1ccccc1I ; CCOC(=O)c1ccccc1I]

In a 5 L fixed glass assembly, Ethanol (1.25 L) was charged at room temperature. 2-iodobenzoic acid (XI-1 a) (250 g, 1.00 mol) was added in one lot at room temperature. Sulphuric acid (197.7 g, 2.01 mol) was added carefully in to reaction mixture at 20 to 35° C. Heated the reaction mixture to 80 to 85° C. Reaction mixture was stirred for 20 hours at 80 to 85° C. After completion of reaction distilled out ethanol at below 60° C. Cooled the reaction mixture to room temperature. Water (2.5 L) was then added carefully at 20 to 35° C. The reaction mixture was then charged with Ethyl acetate (1.25 L). Upon completion of Ethyl acetate addition, reaction mixture turns out to be clear solution. At room temperature it was stirred for 5 to 10 minutes and separated aqueous layer. Aqueous layer then again extracted with ethyl acetate (1.25 L) and separated aqueous layer.

Combined organic layer then washed with twice 10% sodium bicarbonate solution (2×1.25 L) and twice process water (2×1.25L) and separated aqueous layer. Organic layer then washed with 30% brine solution (2.5 L) and separated aqueous layer. Concentrated ethyl acetate in vacuo to get ethyl 2-iodobenzoate (XI-a) in 95% yield, as an oil, which was used in next the reaction, without any further purification.

Step-4. Preparation of ethyl 2-(butoxy(tert-butoxycarbonyl)amino)benzoate (XIX-5)

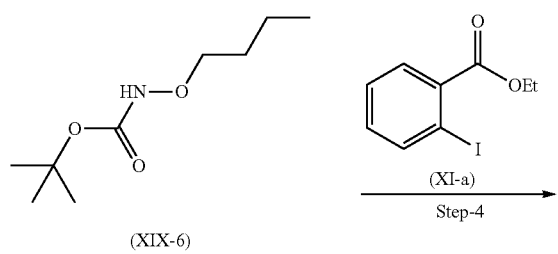

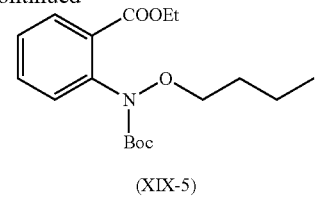

To a stirring solution of Copper (I) iodide (4.02 g, 0.021 mol) in a solvent of Toluene (400 ml) was added Glycine (10.31 g, 0.137 mol), Ethyl 2-iodobenzoate (58.35 g, 0.211 mol), tert-butyl butoxycarbamate (XIX-6) (40.0 g, 0.211 mol), Potassium carbonate (233.7 g, 1.69 mol) and Ethanol (240 ml) at 25° C. to 35° C. Reaction mixture was stirred at 78° C. to 83° C. for 24 h. Cool the reaction mixture to room temperature. Charge Ethyl acetate in to reaction mixture and stirred for 30 minutes. Hyflow filter the reaction mixture and washed with Ethyl acetate. Washed filtrate with water followed by brine solution and separated organic layer. Evaporated solvent under reduced pressure to get ethyl 2-(butoxy (tert-butoxycarbonyl)amino)benzoate (XIX-5) as a yellow colored liquid with 84% yield.

Step-5. Preparation of ethyl 2-(butoxyamino)benzoate (XIX-4):

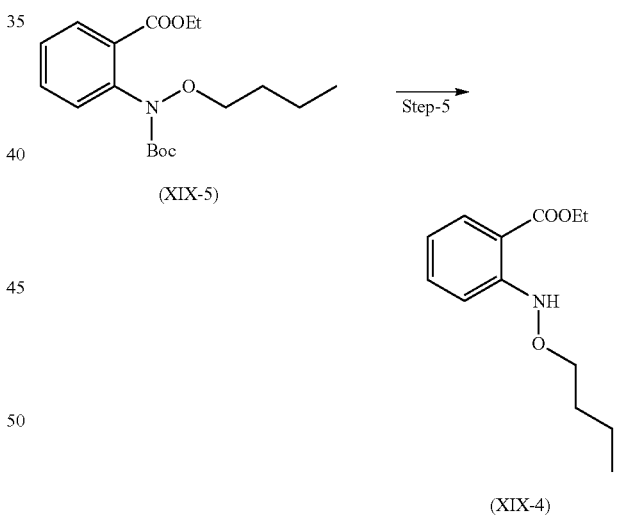

A solution of ethyl 2-(butoxy(tert-butoxycarbonyl)amino) benzoate (XIX-5) (15.0 g, 0.044 mol) in Dichloromethane (120 ml) was treated under stirring with Methanolic HCl (53.08 g, 0.266 mol) (% HCl in methanol is 18.34% w/w) at 0° C. to 10° C. Reaction mixture was stirred at 25° C. to 35° C. for 3 hours. Reaction mixture was then diluted with water. The organic layer was washed with brine and separated organic layer. Evaporated solvent under reduced pressure to get ethyl 2-(butoxyamino)benzoate (XIX-4) as a yellow colored liquid with 85% yield.

Step-6. Preparation of ethyl 2-(N-butoxy-3-ethoxy-3-oxopropanamido)benzoate (XIX-3)

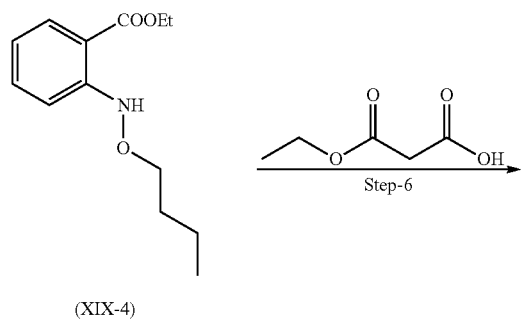

(XIX-4)

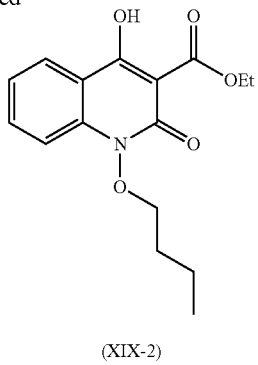

(XIX-2)

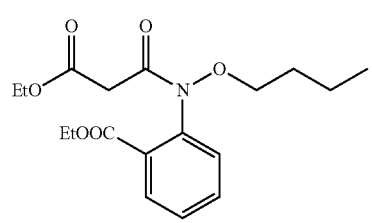

(XIX-3)

To a stirring solution of ethyl 2-(butoxyamino)benzoate (XIX-4) (35 g, 0.147 mol) and 3-ethoxy-3-oxopropanoic acid (21.4 g, 0.162 mol) in acetonitrile (175 ml) was added pyridine (46.7 g, 0.590 mol) and reaction mixture was cooled to 0 to 5° C. To this was added POCl$_3$ (24.88 g, 0.162 mol) at 0 to 5° C. in 1.5 h. and stirring continued for 30 min. Reaction mixture was diluted with water. Extract reaction mixture with Dichloromethane and separated aqueous layer. Dichloromethane layer washed with water and brine solution and separated the aqueous layer. Evaporated solvent under reduced pressure to get ethyl 2-(N-butoxy-3-ethoxy-3-oxopropanamido)benzoate (XIX-3) as a red colored liquid with 98% yield.

Step-7. Preparation of ethyl 1-butoxy-4-hydroxy-2-oxo-1,2-dihydroquinoline-3-carboxylate (XIX-2)

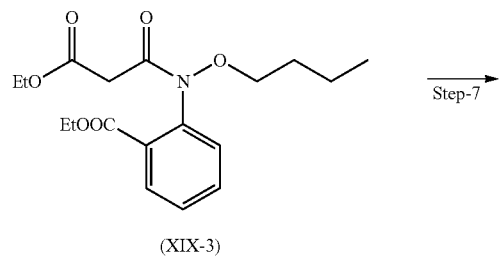

(XIX-3)

To a stirring solution of ethyl 2-(N-butoxy-3-ethoxy-3-oxopropanamido)benzoate (XIX-3) (49 g, 0.139 mol) in a solvent Methanol (220 mL) was added slowly sodium methoxide (10.55 g, 0.195 mol) at 10 to 15° C. Reaction mixture was stirred for 1 h. at 15 to 20° C. Excess methanol was distilled out and then reaction mixture diluted with Hydrochloric acid solution. Precipitated product was filtered and dried to get ethyl 1-butoxy-4-hydroxy-2-oxo-1,2-dihydroquinoline-3-carboxylate (XIX-2) with 89% yield.

Step-8. Preparation of ethyl (1-butoxy-4-hydroxy-2-oxo-1,2-dihydroquinoline-3-carbonyl)glycinate (XIX-1)

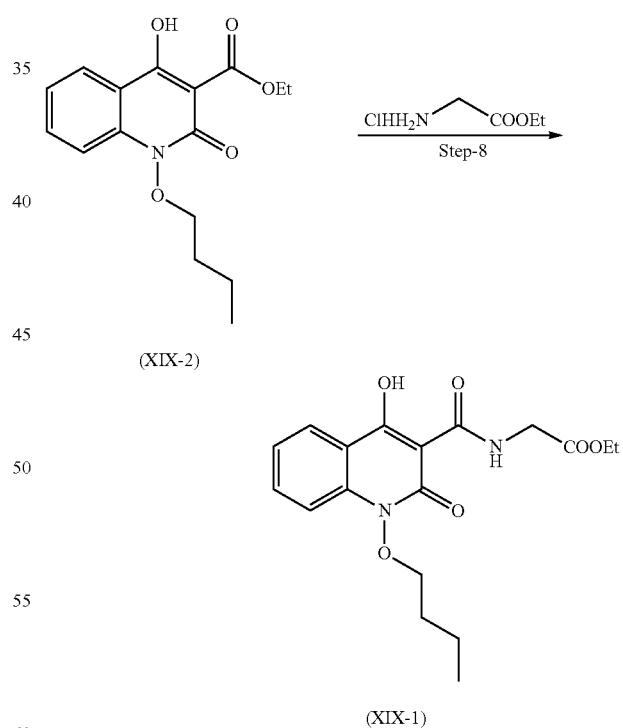

To a stirring solution of ethyl 1-butoxy-4-hydroxy-2-oxo-1,2-dihydroquinoline-3-carboxylate (XIX-2) (26 g, 0.085 mol) in a solvent THF (20.5 ml) was added ethyl glycinate hydrochloride (13.07 g, 0.094 mol) and Diisopropylethyl amine (16.50 g, 0.128 mol) at room temperature. Reaction mixture was stirred for 18 h. at 65 to 70° C. Excess THF was distilled out and then reaction mixture diluted with water. Precipitated product was filtered and dried to get crude compound which was purified using methanol at reflux temperature and filtered product to get ethyl (1-butoxy-4-hydroxy-2-oxo-1,2-dihydroquinoline-3 -carbonyl)glycinate (XIX-1) with 78% yield.

Step-9. Preparation of (1-butoxy-4-hydroxy-2-oxo-1,2-dihydroquinoline-3-carbonyl)glycine (XIX)

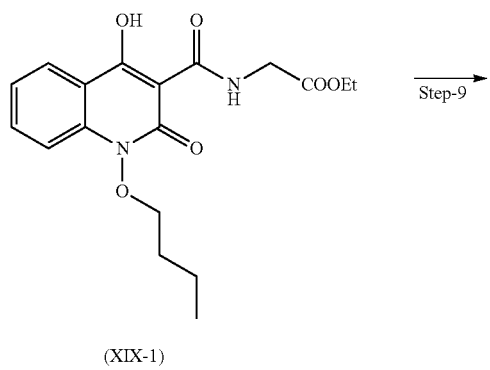

(XIX-1)

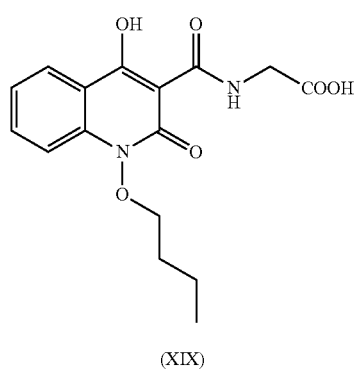

(XIX)

To a stirring solution of ethyl (1-butoxy-4-hydroxy-2-oxo-1,2-dihydroquinoline-3-carbonyl)glycinate (XIX-1) (3.5 g, 0.009 mol) in a solvent methanol (24.5 ml) and water (14 mL) was added sodium hydroxide solution (0.965 g, 0.024 mol) in water (10.5 mL) slowly at room temperature. Reaction mixture was stirred for 30 min. at room temperature. Reaction mixture was acidified using dilute HCl up to pH-2. Precipitated solid was filtered to get (1-butoxy-4-hydroxy-2-oxo-1,2-dihydroquinoline-3-carbonyl)glycine (XIX) with 90% yield.

1H NMR (DMSO-d6): 0.963-1.000 (t, 3H), 1.500-1.575 (m, 2H), 1.764-1.834 (m, 2H), 4.130-4.161 (t, 2H), 4.177-4.194 (d, 2H), 7.389-7.429 (t, 1H), 7.607-7.628 (d, 1H), 7.850-7.893 (t, 1H), 8.084-8.107 (d, 1H), 10.240-10.267 (t, 1H), 12.970 (s, 1H), 16.992 (s, 1H).

The invention claimed is:

1. A process for the preparation of compound of formula (I),

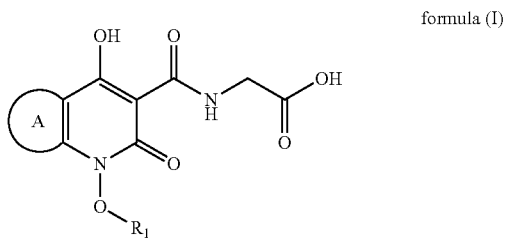

wherein A is optionally substituted aryl ring, $R_1$ represents hydrogen, optionally substituted $(C_1-C_{10})$ alkyl, $(C_3-C_8)$cycloalkyl, $(C_5-C_8)$cycloalkenyl, aryl, cycloalkanylalkyl, heteroaralkyl, heterocyclylalkyl groups, comprising following steps:

Step 1) reacting 2-hydroxyisoindoline-1,3-dione with compound of formula (VII) in presence of appropreate base, solvents and reagents to get compound of formula (VIII) which is further converted to compound of formula (X) after protection with Boc-anhydride;

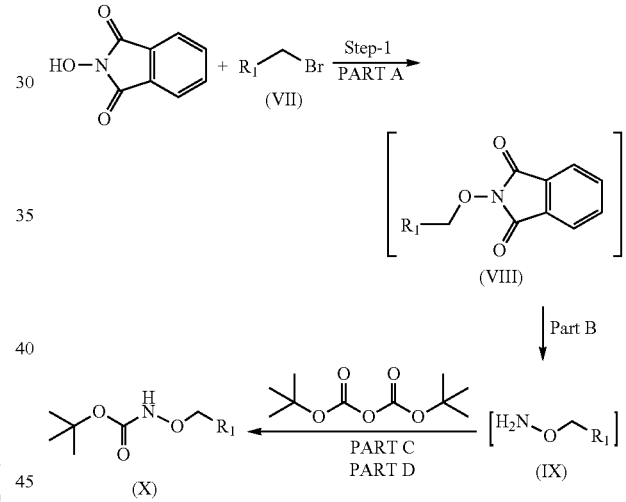

Step 2) reacting compound of formula (X) with compound of formula (XI) with suitable reagent in presence of suitable base and solvent at 78-85° C. temperature range to give compound (XII);

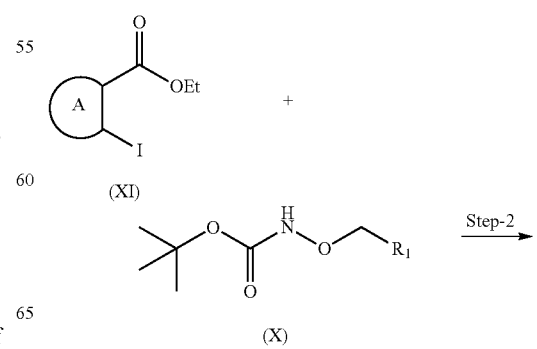

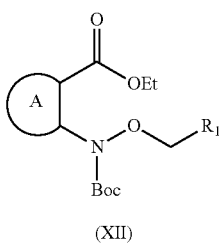

(XII)

Step 3) deprotecting the compound of formula (XII) in presence of suitable reagents to give compound (XIII);

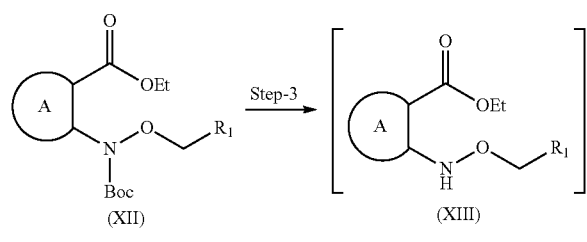

Step 4) reacting compound of formula (XIII) with ethyl hydrogen malonate to give compound of formula (XIV);

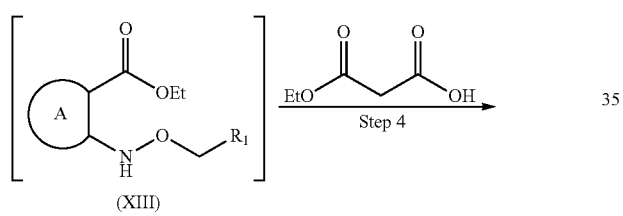

(XIV)

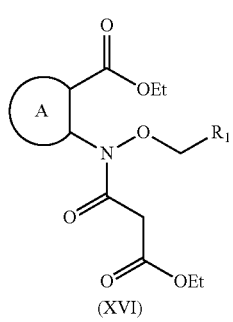

(XVI)

Step 5) reacting compound of formula (XIV) further with suitable reagents such as sodium methoxide and sodium ethoxide and suitable solvents such as methanol, ethanol, dimethyl formamide and DMSO to give compound of formula (XV);

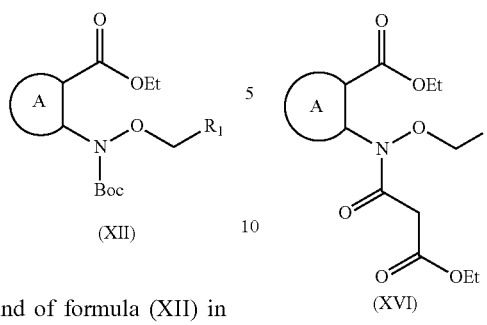

Step 6) reacting compound of formula (XV) with HCl salt of Glycine ethyl ester to give compound of formula (XVI);

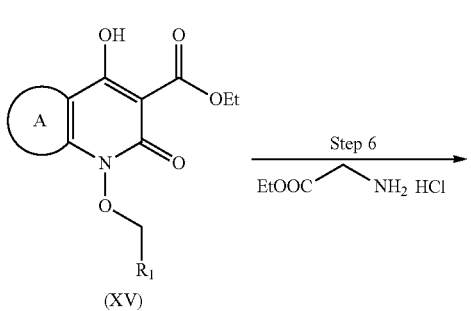

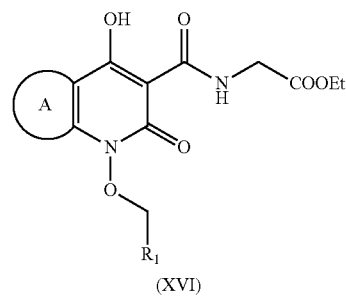

(XVI)

Step 7) reacting compound of formula (XVI) with suitable acid to form compound for formula (I);

(XVI)

formula (I)

2. The process according to claim 1 in step 1, wherein appropriate base is selected from sodium carbonate, Potassium carbonate, sodium hydride, potassium hydroxide, sodium hydroxide, triethyl amine, N,N-diisoppropyl ethyl amine, DBU, DBN and DABCO.

3. The process according to claim 1 in step 1, wherein appropriate solvent is selected from dimethyl sulfoxide, dimethyl formamide, tetrahydrofuran, dichloromethane, ethanol, methanol, toluene, ethyl acetate and acetonitrile.

4. The process according to claim 1 in step 1, wherein appropriate reagents are selected from hydrazine hydrate, methyl hydrazine, ammonia (for part B), Boc.-anhydride (for part C) and imidazole (for part D).

5. The process according to claim 1 in step 2, wherein reagents are copper iodide and glycine.

6. The process according to claim 1 in step 2, wherein base is selected from caesium carbonate, potassium carbonate, sodium tert-butoxide and potassium phosphate tribasic.

7. The process according to claim 1 in step 2, wherein solvent is selected from toluene, dimethyl formamide, 1,4-dioxane, dimethoxyethane, ethanol, methanol, isopropyl alcohol, butanol and mixture of solvent.

8. The process according to claim 1 in step 3, wherein reagent used for deprotection is selected from methanolic HCl, isopropyl HCl, ethanolic HCl and alcoholic solution of p-toluene sulphonic acid.

9. The process according to claim 1 in step 4, wherein reagent is phosphorous oxychloride.

10. The process according to claim 1 in step 4, wherein base is selected from triethyl amine, pyridine and N, N-diisopropyl ethyl amine.

11. The process according to claim 1 in step 4, wherein solvent is selected from dichloromethane, acetonitrile and toluene.

12. The process according to claim 1 in step 5, wherein reagent is selected from sodium methoxide and sodium ethoxide.

13. The process according to claim 1 in step 5, wherein acid for neutralization is selected from aq. Hydrochloric acid, citric acid, acetic acid and sulphuric acid.

14. The process according to claim 1 in step 5, wherein solvent is selected from methanol, ethanol, dimethyl formamide and DMSO.

15. The process according to claim 1 in step 6, wherein base is selected from N, N-diisopropylethyl amine and triethyl amine.

16. The process according to claim 1 in step 6, wherein solvent is selected from 1,4-dioxane, acetonitrile, tetrahydrofuran, ethyl acetate, toluene, methanol and ethanol.

17. The process according to claim 1 in step 7, wherein base is selected from sodium hydroxide, lithium hydroxide, potassium hydroxide.

18. The process according to claim 1 in step 7, wherein acid for acidification is selected from hydrochloric acid, citric acid, sulphuric acid and acetic acid.

19. A process for the preparation of compound of formula (I-a), (I-a)

comprising following steps:

Step 1a) reacting 2-hydroxyisoindoline-1,3-dione with (bromomethyl)cyclopropane VII-a) in presence of appropreate base, solvents and reagents to get 2-(cyclopropylmethoxy)isoindoline-1,3-dione (VIII-a) which is further converted to tert-butyl (cyclopropylmethoxy)carbamate (X-a) after protection with Boc-anhydride Step 2a) reacting tert-butyl (cyclopropylmethoxy)carbamate (X-a) with ethyl 2-iodobenzoate (XI-a) with suitable reagent in presence of suitable base and solvent at 78-85° C. temperature range to give compound (XII-a)

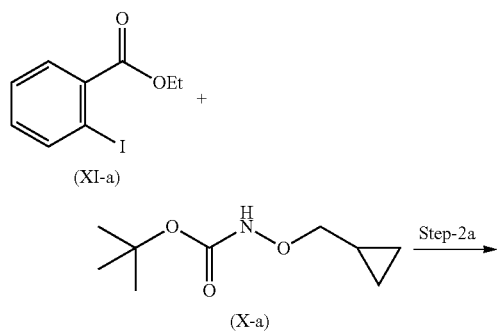

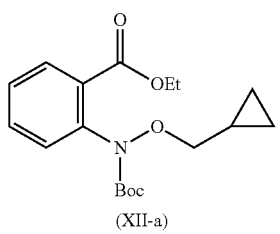

Step 3a) Deprotecting the compound ethyl 2-((tert-butoxycarbonyl)(cyclopropylmethoxy)amino)benzoate (XII-a) in presence of suitable reagents such as alcoholic solution of acid to give ethyl 2-((cyclopropylmethoxy)amino)benzoate (XIII-a)

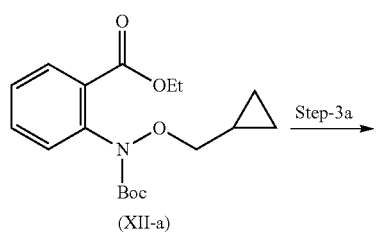

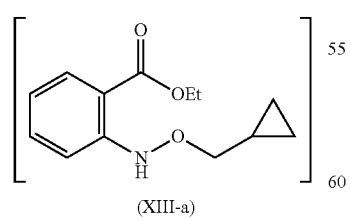

Step 4a) reacting ethyl 2-((cyclopropylmethoxy)amino)benzoate (XIII-a) with ethyl hydrogen malonate to give ethyl 2-(N-(cyclopropylmethoxy)-3-ethoxy-3-oxopropanamido)benzoate (XIV-a)

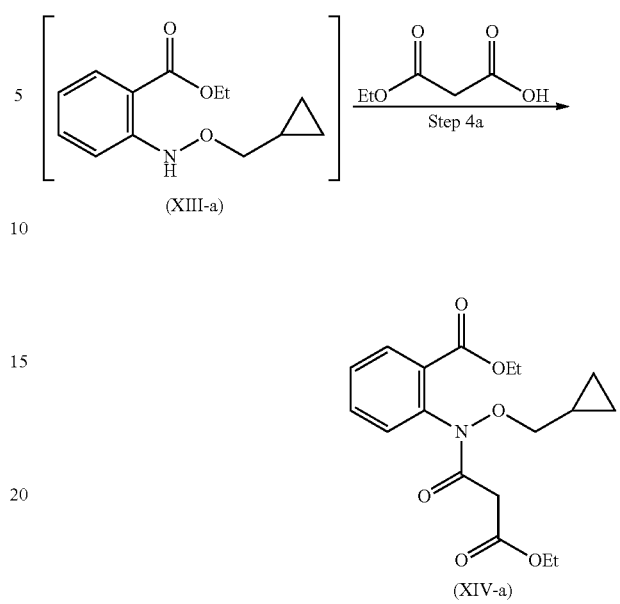

Step 5a) reacting ethyl 2-(N-(cyclopropylmethoxy)-3-ethoxy-3-oxopropanamido)benzoate (XIV-a) further with suitable reagents sodium methoxide and sodium ethoxide and solvents to give ethyl 1-(cyclopropylmethoxy)-4-hydroxy-2-oxo-1,2-dihydroquinoline-3-carboxylate (XV-a)

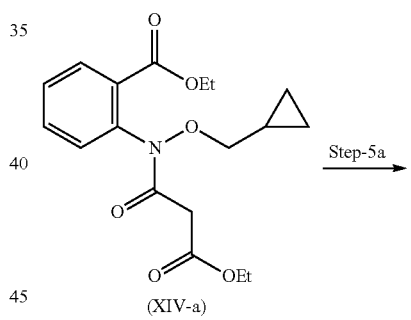

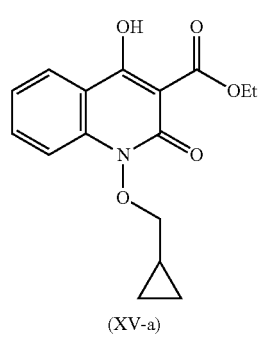

Step 6a) reacting ethyl 1-(cyclopropylmethoxy)-4-hydroxy-2-oxo-1,2-dihydroquinoline-3-carboxylate (XV-a) with HCl salt of Glycine ethyl ester to give ethyl (1-(cyclopropylmethoxy)-4-hydroxy-2-oxo-1,2-dihydroquinoline-3-carbonyl)glycinate (XVI-a)

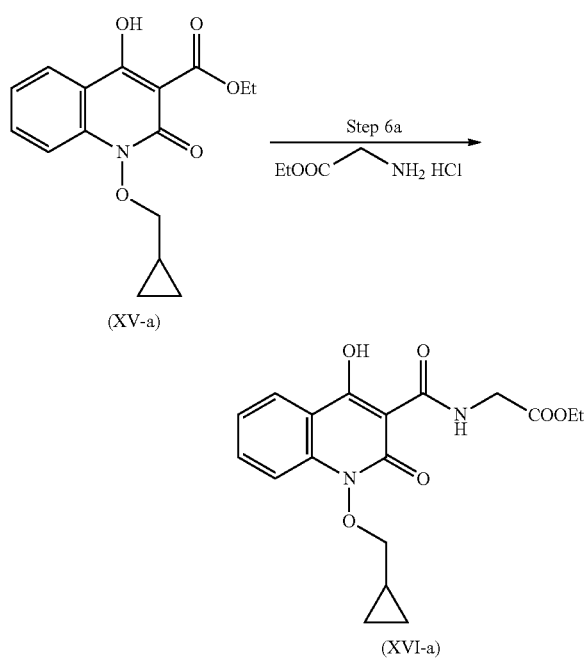

Step 7a) hydrolyzing ethyl (1-(cyclopropylmethoxy)-4-hydroxy-2-oxo-1,2-dihydroquinoline-3-carbonyl) glycinate (XVI-a) with suitable acid to get compound of formula (I-a)

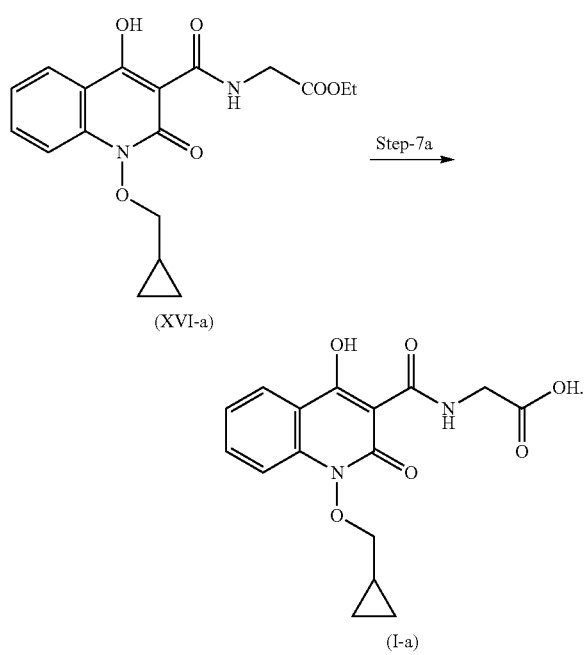

20. The process according to claim 19 in step (1a), wherein appropriate base is selected from sodium carbonate, potassium carbonate, sodium hydride, potassium hydroxide, sodium hydroxide, triethyl amine, N,N-diisoppropyl ethyl amine, DBU, DBN and DABCO.

21. The process according to claim 19 in step (1a), wherein appropriate solvent is selected from dimethyl sulfoxide, dimethyl formamide, tetrahydrofuran, dichloromethane, ethanol, methanol, toluene, ethyl acetate and acetonitrile.

22. The process according to claim 19 in step (1a), wherein appropriate reagents are selected from hydrazine hydrate, methyl hydrazine, ammonia (for part B'), Boc.-anhydride (for part C') and imidazole (for part D').

23. The process according to claim 19 in step (2a), wherein reagents are copper (I) iodide.

24. The process according to claim 19 in step (2a), wherein ligands are selected from glycine, proline, 1,10-phenanthroline.

25. The process according to claim 19 in step 2a, wherein base is selected from caesium carbonate, potassium carbonate, sodium tert-butoxide and potassium phosphate tribasic.

26. The process according to claim 19 in step 2a, wherein solvent is selected from toluene, dimethyl formamide, 1,4-dioxane, dimethoxyethane, ethanol, methanol, isopropyl alcohol, butanol.

27. The process according to claim 19 in step 3a, wherein reagent used for deprotection is selected from methanolic HCl, isopropolic HCl, ethanolic HCl and alcoholic solution of p-toluene sulphonic acid.

28. The process according to claim 19 in step 4a, wherein reagent is phosphorous oxychloride.

29. The process according to claim 19 in step 4a, wherein base is selected from triethyl amine, pyridine and N, N-diisopropylethyl amine.

30. The process according to claim 19 in step 4a, wherein solvent is selected from dichloromethane, acetonitrile and toluene.

31. The process according to claim 19 in step 5a, wherein reagent is selected from sodium methoxide and sodium ethoxide.

32. The process according to claim 19 in step 5a, wherein acid for neurtralization is selected from aq. Hydrochloric acid, citric acid, acetic acid and sulphuric acid.

33. The process according to claim 19 in step 5a, wherein solvent is selected from methanol, ethanol, dimethyl formamide and DMSO.

34. The process according to claim 19 in step 6a, wherein base is selected from N, N-diisopropylethyl amine and triethyl amine.

35. The process according to claim 19 in step 6a, wherein solvent is selected from 1,4-dioxane, acetonitrile, tetrahydrofuran, ethyl acetate, toluene, methanol and ethanol.

36. The process according to claim 19 in step 7a, wherein base is selected from sodium hydroxide, lithium hydroxide, potassium hydroxide.

37. The process according to claim 19 in step 7a, wherein acid for acidification is selected from hydrochloric acid, citric acid, sulphuric acid and acetic acid.

38. An intermediate of formula (XII-a)

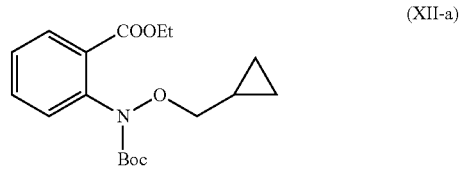 [SMILES: CCOC(=O)c1ccccc1N(OCC1CC1)C(=O)OC(C)(C)C]

having following properties:
1H NMR: $^1$H NMR (CDCl$_3$): 0.26-0.23 (m, 2H), 0.52-0.48 (m, 2H), 1.10-1.08 (m, 1H), 1.38-1.35 (t, 3H), 1.51

(s, 9H), 3.78-3.76 (d, J=7.6 Hz, 2H), 4.35-4.30 (q, J=6.8 Hz, 2H), 7.29-7.25 (m, 1H), 7.49-7.47 (m, 2H), 7.78-7.77 (d, 1H).

39. The process for preparation of intermediate compound of formula (XII-a) comprising following steps:

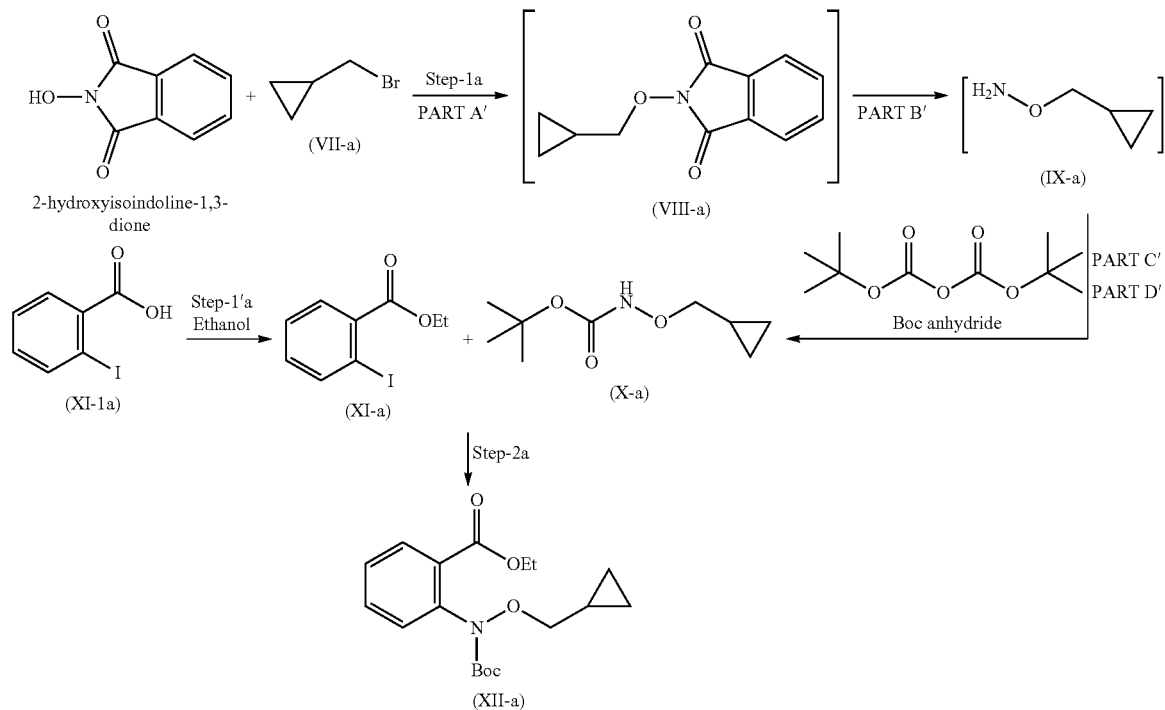

Step 1a) reacting 2-hydroxyisoindoline-1,3-dione with (bromomethyl)cyclopropane (VII-a) in presence of appropreate base, solvents and reagents to get 2-(cyclopropylmethoxy)isoindoline-1,3-dione (VIII-a) which is further converted to tert-butyl (cyclopropylmethoxy)carbamate (X-a) after protection with Boc-anhydride

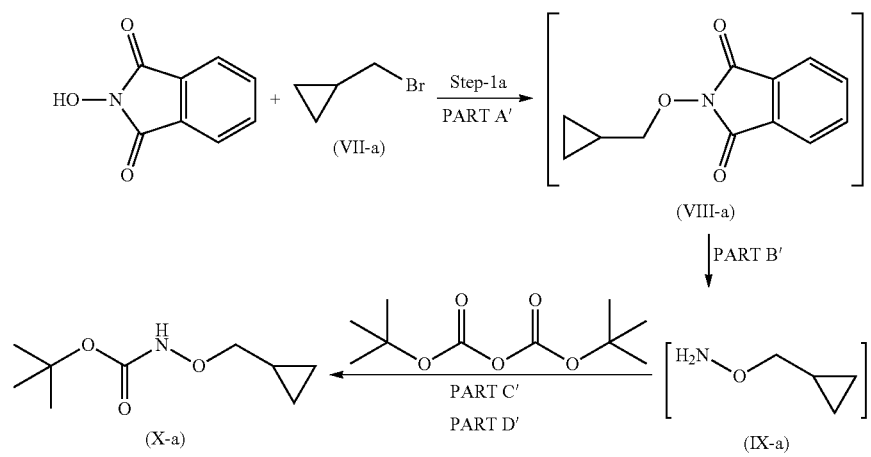

Step 2a) reacting tert-butyl (cyclopropylmethoxy)carbamate (X-a) with ethyl 2-iodobenzoate (XI-a) and suitable reagent in presence of suitable base and solvent at 78-85° C. to give compound (XII-a)

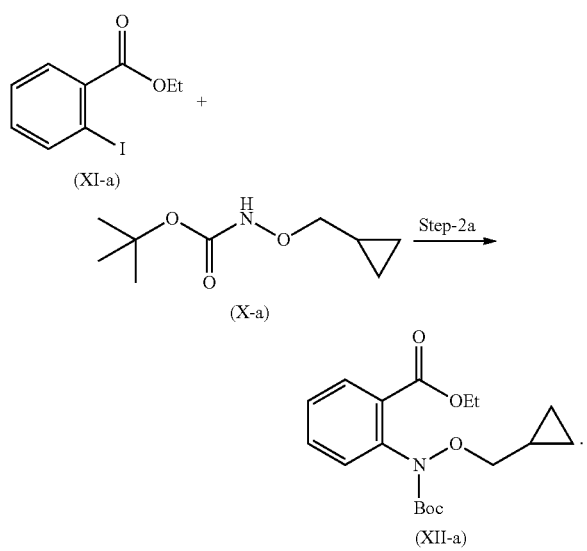

(XI-a)

(X-a)

Step-2a (XII-a)

40. The process according to claim 39 in step 1 a, wherein appropriate base is selected from sodium carbonate, potassium carbonate, sodium hydride, potassium hydroxide, sodium hydroxide, triethyl amine, N,N-diisoppropyl ethyl amine, DBU, DBN and DABCO.

41. The process according to claim 39 in step 1a, wherein appropriate solvent is selected from dimethyl sulfoxide, dimethyl formamide, tetrahydrofuran, dichloromethane, ethanol, methanol, toluene, ethyl acetate and acetonitrile.

42. The process according to claim 39 in step 1a, wherein appropriate reagents are selected from hydrazine hydrate, methyl hydrazine, ammonia (for part B'), Boc.-anhydride (for part C') and imidazole (for part D').

43. The process according to claim 39 in step 2a, wherein reagents are copper (I) iodide.

44. The process according to claim 39 in step (2a), wherein ligands are selected from glycine, proline, 1,10-phenanthroline.

45. The process according to claim 39 in step 2a, wherein base is selected from caesium carbonate, potassium carbonate, sodium tert-butoxide and potassium phosphate tribasic.

46. The process according to claim 39 in step 2a, wherein solvent is selected from toluene, dimethyl formamide, 1,4-dioxane, dimethoxyethane, ethanol, methanol, isopropyl alcohol, butanol.

47. A crystalline compound of formula (I-a)

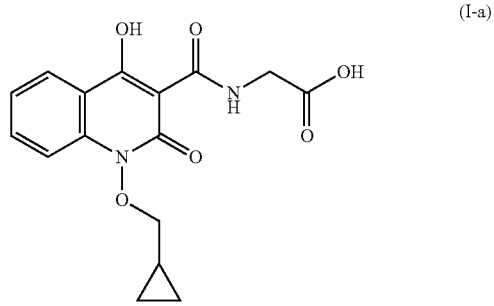 [SMILES: O=C(O)CNC(=O)c1c(O)c2ccccc2n(OCC2CC2)c1=O]

(I-a)

having a powder X-ray diffraction pattern as shown in FIG. 1.

48. A crystalline compound of formula (I-a) having at least three of characteristic powder X-ray diffraction pattern peaks expressed at about 8.0, 8.9, 10.6, 11.3, 16.1, 25.5, 26.4±0.2 degree 2 theta.

49. The compound of formula (XVII).

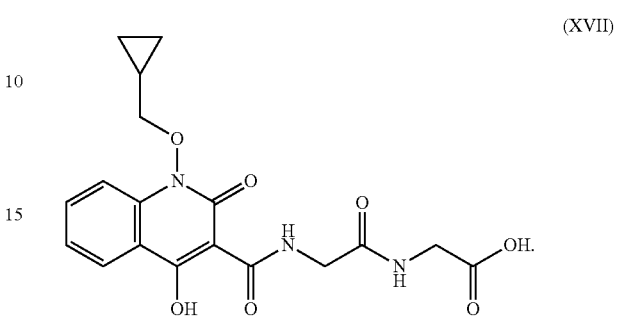

(XVII)

50. The compound of formula (XVII) as claimed in claim 47 is controlled in formula (I-a) with the limit of not more than 0.20%.

51. The compound of formula (XVIII).

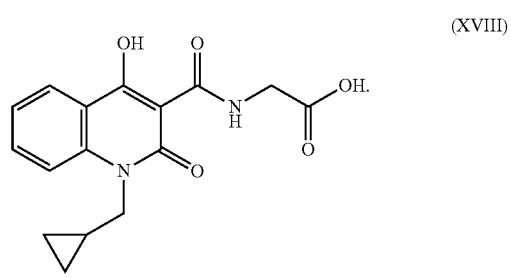 [SMILES: O=C(O)CNC(=O)c1c(O)c2ccccc2n(CC2CC2)c1=O]

(XVIII)

52. The compound of formula (XVIII) as claimed in claim 49 is controlled in formula (I-a) with the limit of not more than 0.30%.

53. The compound of formula (XIX).

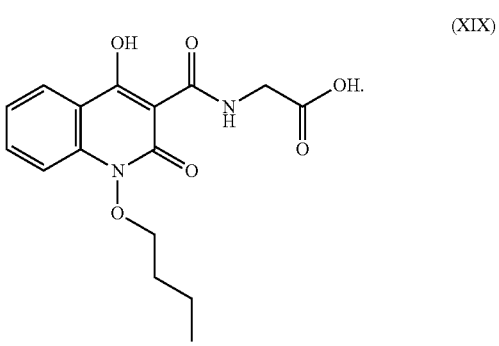 [SMILES: CCCCOn1c(=O)c(C(=O)NCC(=O)O)c(O)c2ccccc21]

(XIX)

54. The compound of formula (XIX) as claimed in claim 51 is controlled in formula (I-a) with the limit of not more than 0.15%.

55. A crystalline compound of formula (I-a) having characteristic powder X-ray diffraction pattern peaks expressed at about 8.0, 8.9, 10.6, 11.3, 16.1, 25.5, 26.4±0.2 degree 2 theta.

* * * * *